United States Patent
Galcera-Contour et al.

(10) Patent No.: US 7,795,284 B2
(45) Date of Patent: Sep. 14, 2010

(54) 4,7-DIOXOBENZOTHIAZOLE-2-CARBOXAMIDE DERIVATIVES, THEIR PREPARATION AND THEIR THERAPEUTIC USES

(75) Inventors: Marie-Odile Galcera-Contour, Bondoufle (FR); Grégoire Prevost, Antony (FR); Alban Sidhu, Palaiseau (FR)

(73) Assignee: Ipsen Pharma S.A.S., Paris (FR)

( * ) Notice: Subject to any disclaimer, the term of this patent is extended or adjusted under 35 U.S.C. 154(b) by 502 days.

(21) Appl. No.: 11/718,791

(22) PCT Filed: Nov. 7, 2005

(86) PCT No.: PCT/FR2005/002763

§ 371 (c)(1),
(2), (4) Date: May 7, 2007

(87) PCT Pub. No.: WO2006/051202

PCT Pub. Date: May 18, 2006

(65) Prior Publication Data

US 2007/0244186 A1    Oct. 18, 2007

(30) Foreign Application Priority Data

Nov. 5, 2004   (FR) ................. 04 11802

(51) Int. Cl.
*A61K 31/428* (2006.01)
*A61K 31/496* (2006.01)
*C07D 277/60* (2006.01)
*C07D 417/02* (2006.01)

(52) U.S. Cl. .............. 514/367; 548/152; 548/178; 544/358; 544/368; 514/252.13; 514/365

(58) Field of Classification Search ........... 548/152, 548/178; 544/358, 359, 368; 514/252.12, 514/252.13, 365, 367
See application file for complete search history.

(56) References Cited

U.S. PATENT DOCUMENTS

| | | | |
|---|---|---|---|
| 5,523,430 A | 6/1996 | Patel et al. | |
| 7,279,467 B2 | 10/2007 | Contour et al. | |
| 7,335,674 B2 | 2/2008 | Contour et al. | |
| 7,495,021 B2 * | 2/2009 | Contour et al. | 514/367 |
| 2006/0135573 A1 | 6/2006 | Contour et al. | |
| 2006/0281736 A1 | 12/2006 | Prevost et al. | |
| 2007/0293487 A1 | 12/2007 | Contour et al. | |

FOREIGN PATENT DOCUMENTS

| | | |
|---|---|---|
| GB | 1 534 275 | 11/1978 |
| WO | WO 97/30053 | 2/1997 |
| WO | WO 01/34203 | 5/2001 |
| WO | WO 01/45680 | 6/2001 |
| WO | WO 03/050098 | 6/2003 |
| WO | WO 03/055868 A1 | 7/2003 |
| WO | WO 2005/000843 | 1/2005 |
| WO | WO 2005/000852 | 1/2005 |
| WO | WO 2006/051202 | 5/2006 |
| WO | WO 2006/067311 | 6/2006 |

OTHER PUBLICATIONS

Ryu et al., "Synthesis and Antifungal Activities of 5/6-arylamino-4,7-Dioxobenzothiazoles", Bio-Organic and Medicinal Chemistry Letters, vol. 10, No. 14, pp. 1589-1591, (Jul. 17, 2000).
Ryu et al., "5-Arylamino-2-methyl-4,7 Dioxobenzothiazoles as Inhibitors of Cyclin-Dependent Kinase 4 and Cytocoxic Agents", Bio-Organic and Medicinal Chemistry Letters, vol. 10, No. 5, pp. 461-464, (Mar. 5, 2000).
Lyon et al., "Synthesis and Structure Verification of an Analogue of Kuanoniamine A," J.Chem. Soc. Perkin Transactions 1: Organic and BioOrganic Chemistry, vol. 4; pp. 437-442 (1999).
Kristjansdottir et al., "Cdc25 Phosphatases and Cancer", Chemistry and Biology, vol. 11, pp. 1043-1051 (Aug. 2004).
Ryu et al., "Modulation of NAD(P)H: Quinone Qxidoreductase (NQO1) Activity Mediated by 5-arylamino-2-methyl-4-7-Dioxobenzothiazoles and their Cytotoxic Potential", Archives of Pharmacal Research, vol. 23, issue 6, pp. 554-558 (2000).
Eckstien, J.W., "Cdc25 as a Potential Target of Anticancer Agents" Investigational New Drugs, vol. 18, pp. 149-156, Figure 3a (2000).
McCain, D.F. et al., Suramin Derivatives as Inhibitors and Activators of Protein-Tyrosine Phosphates, Jpurnal of Biological Chemistry, vol. 129, No. 15, pp. 14713-14725, Figures 2-6 (Jan. 2004).
Talaga, P. et al., "Synthesis of Boc-Cys_Ala_OMe and its Stereoselective Addiction to α-Methylene-γ-Butrolactones", Tetrahedron, vol. 45, No. 16, pp. 5029-5038 (1989).
Zhu, X. et al. "Synthesis of S-Linked Glycopeptides in Aqueos Solution". J. Org. Chem., vol. 68, No. 14, pp. 5641-5651, XP002326455, Schema 1 (2003).
Golub et al., "Molecular Classification of Cancer: Class Discovery and Class Prediction by Gene Expression Monitoring", Science, vol. 286, pp. 531-537 (1999).
Hortobagyi, G. "Treatment of Breast Cancer", N. Engl., J. Med, 339, pp. 974-984 (1998).
Journal of Chemical Society, 1928, 2313-2320.
FR 1 495 752 published in 1967.
Biological Pharmacology, 1976, 25 (24), 2747-2750.
Journal of American Chemical Society, 1922, 826-837.
Proceedings of the Society for Experimental Biology and Medicine, 1947, 66, 362-365.
Antibiotics and Chemotherapy (Washington DC), 1958, 8, 33-36.
Journal of Organic Chemistry, 1979, 44, 99-104.
European Journal of Medicinal Chemistry, 1989, 24 (6), 639-641.
Preliminary Amendment Filed Jun. 18, 2007 in Co-pending U.S. Appl. No. 11/722,075.

* cited by examiner

*Primary Examiner*—Golam M Shameem
(74) *Attorney, Agent, or Firm*—Hunton & Williams LLP

(57) ABSTRACT

A subject of the present invention is 4,7-dioxobenzothiazole-2-carboxamide derivatives, which inhibit the cdc25 phosphatases, in particular cdc25-C phosphatase. These compounds can in particular be used in the treatment of cancer.

12 Claims, No Drawings

4,7-DIOXOBENZOTHIAZOLE-2-CARBOXAMIDE DERIVATIVES, THEIR PREPARATION AND THEIR THERAPEUTIC USES

CROSS-REFERENCE TO RELATED APPLICATIONS

This application claims priority to International Application No. PCT/FR2005/002763, filed on Nov. 7, 2005, which in turn claims priority to Application No. FR 0411802, filed on Nov. 5, 2004, the disclosures of which are herein incorporated by reference in their entirety.

FIELD OF INVENTION

A subject of the present invention is novel 4,7-dioxobenzothiazole-2-carboxamide derivatives, which inhibit the cdc25 phosphatases, in particular cdc25-C phosphatase.

BACKGROUND OF INVENTION

Control of the transition between the different phases of the cell cycle during mitosis or meiosis is ensured by a set of proteins the enzymatic activities of which are associated with different states of phosphorylation. These states are controlled by two major classes of enzymes: the kinases and the phosphatases.

The synchronization of the different phases of the cell cycle thus allows the reorganization of the cell architecture at each cycle throughout the living world (microorganisms, yeast, vertebrates, plants). Among the kinases, the cycline-dependent kinases (CDKs) play a major role in this control of the cell cycle. The enzymatic activity of these different CDKs is controlled by two other families of enzymes which work in opposition (Jessus and Ozon, *Prog. Cell Cycle Res.* (1995), 1, 215-228). The first includes kinases such as Wee1 and Mik1 which deactivate the CDKs by phosphorylating certain amino acids (Den Haese et al., *Mol. Biol. Cell* (1995), 6, 371-385). The second includes phosphatases such as Cdc25 which activate the CDKs by dephosphorylating the tyrosine and threonine residues of CDKs (Gould et al., *Science* (1990), 250, 1573-1576).

The phosphatases are classified in 3 groups: the serine/threonine phosphatases (PPases), the tyrosine phosphatases (PTPases) and the dual-specificity phosphatases (DSPases). These phosphatases play an important role in the regulation of numerous cell functions.

As regards human cdc25 phosphatases, 3 genes (cdc25-A, cdc25-B and cdc25-C) code for the cdc25proteins. Moreover, variants originating from the alternative splicing of the gene cdc25B have been identified: these are cdc25B1, cdc25B2 and cdc25B3 (Baldin et al., *Oncogene* (1997), 14, 2485-2495).

The role of the Cdc25 phosphatases in oncogenesis is now better known and the action mechanisms of these phosphatases are illustrated in particular in the following references: Galaktionov et al., *Science* (1995), 269, 1575-1577; Galaktionov et al., *Nature* (1996), 382, 511-517; and Mailand et al., *Science* (2000), 288, 1425-1429.

In particular, the overexpression of the different forms of cdc25 is now reported in numerous series of human tumors:
Breast cancer: cf. Cangi et al., *Résumé* 2984, AACR meeting San Francisco, 2000);
Lymphomas: cf. Hernandez et al., *Int. J. Cancer* (2000), 89, 148-152 and Hernandez et al., *Cancer Res.* (1998), 58, 1762-1767;
Cancers of the neck and the head: cf. Gasparotto et al., *Cancer Res.* (1997), 57, 2366-2368.

Moreover, E. Sausville's group reports an inverse correlation between the level of expression of cdc25-B in a panel of 60 lines and their sensitivities to CDK inhibitors, suggesting that the presence of cdc25 can provide resistance to certain antineoplastic agents and more particularly to CDK inhibitors (Hose et al., *Proceedings of AACR*, Abstract 3571, San Francisco, 2000).

Among other targets, the pharmaceutical industry is therefore currently researching compounds capable of inhibiting the Cdc25 phosphatases in order to use them in particular as anti-cancer agents.

The Cdc25 phosphatases also play a role in the neurodegenerative diseases such as Alzheimer's disease (cf. Zhou et al., *Cell Mol. Life Sci.* (1999), 56(9-10), 788-806; Ding et al., *Am. J. Pathol.* (2000), 157(6), 1983-90; Vincent et al., *Neuroscience* (2001), 105(3), 639-50) so that it is also possible to envisage using compounds possessing an inhibition activity on these phosphatases for treating these diseases.

Another problem addressed by the invention is research into medicaments intended to prevent or treat the rejection of organ transplants or also to treat auto-immune diseases. In these disorders/diseases, the non-appropriate activation of the lymphocytes and the monocytes/macrophages is involved. Immunosuppressive medicaments known at present have side-effects which could be reduced or modified by products specifically targeting the signalling routes in the haematopoietic cells which initiate and maintain inflammation.

Firstly, a subject of the invention is novel inhibitors of cdc25 phosphatases (in particular of cdc25-C phosphatase), which are 4,7-dioxobenzothiazole-2-carboxamide derivatives and correspond to the general formula (I) defined hereafter. Given the above, these compounds are capable of being used as medicaments, in particular in the treatment and/or the prevention of the following diseases or disorders:
inhibition of tumor proliferation alone or in combination with other treatments;
inhibition of normal cell proliferation alone or in combination with other treatments;
neurodegenerative diseases such as Alzheimer's disease;
prevention of spontaneous alopecia;
prevention of alopecia induced by exogenous products;
prevention of radiation-induced alopecia;
prevention of the spontaneous or induced apoptosis of normal cells;
prevention of meiosis and/or fertilization;
prevention of the maturation of the oocytes;
all the diseases/all the disorders corresponding to uses reported for CDK inhibitors, and in particular non-tumorous proliferative diseases (for example: angiogenesis, psoriasis or restenosis), tumorous proliferative diseases, parasitology (proliferation of protozoans), viral infections, neurodegenerative diseases, myopathies; and/or
all diseases/all disorders corresponding to clinical uses of vitamin K and its derivatives.

Moreover, the compounds of the present invention are also, because of their inhibition properties on the cdc25 phosphatases, capable of being used for inhibiting or preventing the proliferation of microorganisms, in particular yeasts. One of the advantages of these compounds is their low toxicity on healthy cells.

DETAILED DESCRIPTION OF THE INVENTION

Firstly, a subject of the invention is the compounds corresponding to general formula (I)

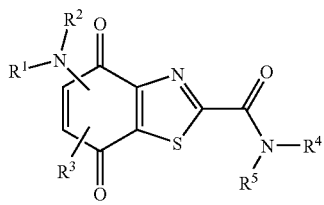 (I)

in racemic, enantiomeric form or any combination of these forms, in which:

$R^1$ represents a hydrogen atom or an alkyl, alkoxyalkyl, alkylthioalkyl, cycloalkyl, —(CH$_2$)—X—Y, —(CH$_2$)—Z—NR$^6$R$^7$ radical or a —CHR$^8$R$^9$ radical, X representing a bond or a linear or branched alkylene radical containing 1 to 5 carbon atoms, Y representing a saturated cyclic carbon system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —CHR$^{10}$—, —CO—, —NR$^{11}$—, —O— and —S—, R$^{10}$ representing a hydrogen atom or an alkyl radical and R$^{11}$ representing a hydrogen atom or an alkyl or aralkyl radical, or also Y representing a carbocyclic or heterocyclic aryl radical optionally substituted 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^{12}$ radical and an NR$^{13}$R$^{14}$ radical, R$^{12}$ representing a hydrogen atom or an alkyl or phenyl radical, and R$^{13}$ and R$^{14}$ independently representing alkyl radicals, Z representing a bond or a linear or branched alkylene radical containing 1 to 5 carbon atoms, R$^6$ and R$^7$ being chosen independently from a hydrogen atom, an alkyl, aralkyl radical or —(CH$_2$)$_n$—OH in which n represents an integer from 1 to 6, or R$^6$ representing an alkoxycarbonyl, haloalkoxycarbonyl or aralkoxycarbonyl radical and R$^7$ representing a hydrogen atom or a methyl radical, or also R$^6$ and R$^7$ forming together with the nitrogen atom a heterocycle with 4 to 7 members comprising 1 to 2 heteroatoms, the members necessary for completing the heterocycle being chosen independently from the —CR$^{15}$R$^{16}$—, —O—, —S— and —NR$^{17}$— radicals, R$^{15}$ and R$^{16}$ independently representing each time that they occur a hydrogen atom or an alkyl radical, and R$^{17}$ representing a hydrogen atom or an alkyl or aralkyl radical, or also R$^{17}$ representing a phenyl radical optionally substituted 1 to 3 times by substituents chosen independently from a halogen atom and an alkyl or alkoxy radical, R$^8$ and R$^9$ forming together with the carbon atom which carries them an indanyl or tetralinyl radical, or also R$^8$ and R$^9$ forming together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical;

$R^2$ representing a hydrogen atom or an alkyl or aralkyl radical;

or also $R^1$ and $R^2$ forming together with the nitrogen atom a heterocycle with 4 to 8 members comprising 1 to 2 heteroatoms, the members necessary for completing the heterocycle being chosen independently from the —CR$^{18}$R$^{19}$—, —O—, —S— and —NR$^{20}$— radicals, R$^{18}$ and R$^{19}$ independently representing each time that they occur a hydrogen atom or an alkyl radical, and R$^{20}$ representing a hydrogen atom or an alkyl or aralkyl radical;

$R^3$ represents a hydrogen atom or a halogen atom;

$R^4$ represents an alkyl radical, a haloalkyl radical, a cycloalkyl radical, a cycloalkylalkyl radical, an alkoxyalkyl radical, one of the carbocyclic or heterocyclic aryl or carbocyclic or heterocyclic aralkyl radicals the aryl nucleus of which is optionally substituted 1 to 3 times by substituents chosen independently from the group constituted by a halogen atom, an alkyl radical, an alkoxy radical, a haloalkyl radical and an —SO$_2$—NH$_2$ radical, or also $R^4$ represents one of the —(CH$_2$)$_m$—[O—(CH$_2$)$_p$]$_q$—O-Alk, —(CH$_2$)$_r$—[O—(CH$_2$)$_s$]$_t$—NR$^{21}$R$^{22}$ or —(CH$_2$)$_v$-A radicals in which m, p and s are each independently an integer from 2 to 4, q is an integer from 1 to 4, t is an integer from 0 to 4, r is an integer from 2 to 12 (and preferably an integer from 2 to 8 and in particular an integer from 2 to 6) and v is an integer from 1 to 12 (and preferably an integer from 1 to 8 and in particular an integer from 1 to 6), Alk is an alkyl radical, R$^{21}$ is a hydrogen atom or an alkyl, alkoxycarbonyl or aralkoxycarbonyl radical, R$^{22}$ is a hydrogen atom or an alkyl radical and A is a saturated heterocycle containing 1 to 2 heteroatoms chosen independently from 0, N and S and attached to the —(CH$_2$)$_v$— group by an N or CH member, said saturated heterocycle containing moreover 2 to 6 additional members chosen independently from —CHR$^{23}$—, —CO—, —NR$^{24}$—, —O— and —S—, R$^{23}$ representing a hydrogen atom or an alkyl radical and R$^{24}$ representing a hydrogen atom, an alkyl radical or an alkoxycarbonyl or aralkoxycarbonyl group, or also $R^4$ represents a radical of formula

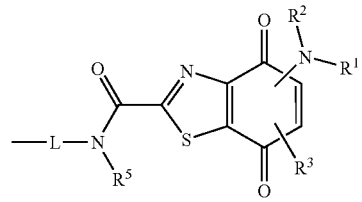

in which $R^1$, $R^2$, $R^3$ and $R^5$ are identical to the $R^1$, $R^2$, $R^3$ radicals mentioned previously and $R^5$ mentioned hereafter, and L is chosen from the —(CH$_2$)$_g$—[O—(CH$_2$)$_w$]$_x$—[O—(CH$_2$)$_y$]$_z$— and —(CH$_2$)$_a$-Ω-(CH$_2$)$_b$— radicals in which g, w and y are integers from 2 to 4 (and preferably 2 to 3), x is an integer from 1 to 3 and z is 0 or 1, a and b are independently integers from 2 to 6 (and preferably 2 to 4) and Ω is chosen from the group constituted by —O—, —S—, —NR—, —CO—, —CO—NR$^{26}$—, —CR$^{27}$R$^{28}$—, a cycloalkylene radical containing 3 to 7 carbon atoms and finally a carbocyclic aryl radical, R$^{25}$ representing an alkyl radical, R$^{26}$ representing a hydrogen atom or a methyl radical, $R^{27}$ and $R^{28}$ each being chosen independently from a hydrogen atom and a methyl group;

or also $R^4$ represents a radical of formula

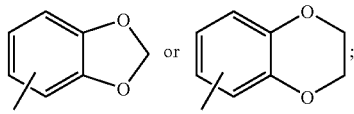

$R^5$ represents a hydrogen atom or an alkyl or aralkyl radical, $R^5$ also being able to represent a radical identical to $R^4$ when $R^4$ represents a carbocyclic or heterocyclic alkyl, haloalkyl, alkoxyalkyl or aralkyl radical, the aryl nucleus of which is optionally substituted 1 to 3 times by substituents chosen independently from the group constituted by a halogen atom, an alkyl radical, an alkoxy radical, a haloalkyl radical and an $-SO_2-NH_2$ radical;

or also $R^4$ and $R^5$ form together with the nitrogen atom which carries them a saturated heterocycle with 4 to 7 members comprising 1 to 2 heteroatoms in total, the members necessary for completing the heterocycle being chosen independently from the $-CR^{29}R^{30}-$, $-O-$, $-S-$ and $-NR^{31}-$ radicals, $R^{29}$ and $R^{30}$ representing a hydrogen atom or an alkyl or aralkyl radical and $R^{31}$ representing $-COR^{32}$ or $-SO_2R^{33}$, $R^{32}$ representing an alkyl radical, a carbocyclic aryl radical optionally substituted 1 to 3 times by substituents chosen independently from the group constituted by a halogen atom, an alkyl radical and an alkoxy radical, or also $R^{32}$ representing a heterocyclic aryl radical or a saturated heterocycle containing 5 to 7 members and 1 to 2 heteroatoms chosen independently from O, N and S (and in particular one of the piperidino, piperazino, morpholino, thiomorpholino or 2-tetrahydrofuryl radicals), $R^{33}$ representing a hydrogen atom or an alkyl radical, or finally $R^4$ and $R^5$ form together with the nitrogen atom which carries them a heterocyclic aryl radical chosen from the radicals

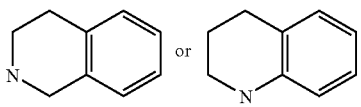

the aromatic ring of which can be substituted 1 to 3 times by substituents chosen independently from the group constituted by an alkyl radical and an alkoxy radical;

and their salts.

The Applicant has surprisingly discovered that the above compounds corresponding to general formula (I) are powerful inhibitors of the cdc25 phosphatases (and in particular of Cdc25C phosphatase), which makes them suitable for use as anti-cancer agents.

The invention therefore relates in the first place to the compounds of general formula (I) defined previously and the salts of such compounds.

By alkyl, unless otherwise specified, is meant a linear or branched alkyl radical containing 1 to 12 carbon atoms, preferably 1 to 10 carbon atoms and more preferentially 1 to 8 carbon atoms (and in particular 1 to 6 carbon atoms).

By alkylene, unless otherwise specified, is meant a linear or branched saturated alkyl radical, containing 1 to 5 carbon atoms, for example a $-CH_2-$ or $-CH_2-CH_2-$ radical.

By alkoxy, unless otherwise specified, is meant a linear or branched alkoxy radical containing 1 to 6 carbon atoms (and in particular 1 to 4 carbon atoms).

By alkoxycarbonyl, unless otherwise specified, is meant a radical of $-CO-O-$alkyl type.

By haloalkoxycarbonyl unless otherwise specified, is meant a radical of $-CO-O-$haloalkyl type.

By haloalkyl, is meant an alkyl radical at least one (and optionally all) of the hydrogen atoms of which is replaced by a halogen atom.

By aralkoxycarbonyl unless otherwise specified, is meant a radical of $-CO-O-$alkyl-aryl type.

By cycloalkyl, unless otherwise specified, is meant a cycloalkyl radical containing 3 to 7 carbon atoms.

By cycloalkylene, unless otherwise specified, is meant a cycloalkyl radical containing 3 to 7 carbon atoms, for example a

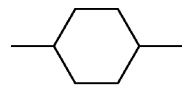

radical.

By alkylthioalkyl, unless otherwise specified, is meant a radical of—alkyl-S-alkyl type.

By carbocyclic or heterocyclic aryl, is meant a carbocyclic or heterocyclic system of 1 to 3 condensed rings comprising at least one aromatic ring, a system being called heterocyclic when at least one of the rings which compose it comprises at least one heteroatom (O, N or ); when a carbocyclic or heterocyclic aryl radical is referred to as substituted, unless otherwise specified, it is meant that said carbocyclic or heterocyclic aryl radical is substituted 1 to 3 times, and preferably from 1 to 2 times by radicals different from a hydrogen atom which, unless otherwise specified, are chosen from a halogen atom and the alkyl or alkoxy radicals; moreover, unless otherwise specified, by aryl is exclusively meant a carbocyclic aryl.

By halogen or atom halogen is meant a chlorine, bromine, fluorine or iodine atom.

By cycloalkylalkyl, alkoxyalkyl, haloalkyl, haloalkoxy and aralkyl radicals, is meant respectively the cycloalkylalkyl, alkoxyalkyl, haloalkyl, haloalkoxy and aralkyl radicals the alkyl, cycloalkyl and aryl radicals of which have the meanings indicated previously.

When it is indicated that a radical is optionally substituted 1 to 3 times, it is preferably optionally substituted 1 to 2 times and more preferentially optionally substituted once.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By haloalkyl, is meant in particular the trifluoromethyl radical. By haloalkoxy, is meant in particular the trifluoromethoxy radical. By carbocyclic aryl, is meant in particular the phenyl and naphthyl radicals. By aralkyl, is meant in particular the phenylalkyl radicals, and in particular the benzyl radical. By saturated cyclic carbon system containing 1 to 3 condensed rings chosen independently from rings with 3 to 7 members, is meant in particular the cyclopropyl, cyclobutyl, cyclohexyl and adamantyl radicals. By heterocyclic aryl or heteroaryl, is meant in particular the thienyl, furanyl, pyrrolyl, imidazolyl, thiazolyl, oxazolyl and pyridyl radicals. Finally, by halogen, is meant the fluorine, chlorine, bromine or iodine atoms.

By salt of a compound, is meant the addition salts of said compound with an organic or inorganic acid or, if appropriate, with a base, and in particular the pharmaceutically acceptable salts of said compound.

By pharmaceutically acceptable salt, is meant in particular addition salts of inorganic acids such as hydrochloride, hydrobromide, hydroiodide, sulphate, phosphate, diphosphate and nitrate or acids organic such as acetate, maleate, fumarate, tartrate, succinate, citrate, lactate, methanesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In certain cases, the compounds according to the present invention can comprise asymmetrical carbon atoms. As a result, the compounds according to the present invention have two possible enantiomeric forms, i.e. the "R" and "S" configurations. The present invention includes the two enantiomeric forms and all combinations of these forms, including the "RS" racemic mixtures. In an effort to simplify matters, when no specific configuration is indicated in the structural formulae, it should be understood that the two enantiomeric forms and their mixtures are represented.

Generally, it is preferred that the saturated heterocycle A is such that it comprises a maximum of 2-CO— members, a maximum of 2 members chosen independently from —$NR^{24}$—, —O— and —S— and a maximum of one —$CHR^{23}$— member in which $R^{23}$ is not a hydrogen atom. Similarly, it is preferred, in the case where $R^4$ and $R^5$ form together with the nitrogen atom which carries them a saturated heterocycle with 4 to 7 members comprising 1 to 2 heteroatoms, that said saturated heterocycle is such that it comprises a maximum of two —$CR^{29}R^{30}$— members in which at least one of $R^{29}$ and $R^{30}$ is not a hydrogen atom.

According to a variant of the invention, the compounds of general formula (I) or their salts are such that $R^4$ does not represent a radical of formula

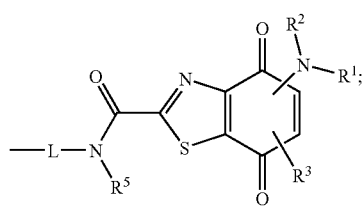

in the remainder of this disclosure, such compounds are called the "compounds of general sub-formula $(I)_M$".

Among the compounds of general sub-formula $(I)_M$, certain will correspond to general sub-formula $(I)_{M5}$

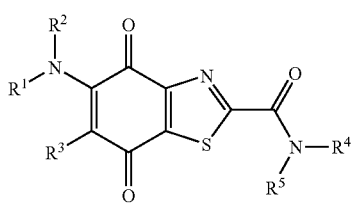

$(I)_{M5}$ in which $R^1$, $R^2$, $R^3$, $R^4$ and $R^5$ have the same meaning as in general sub-formula $(I)_M$; whilst the other will correspond to general sub-formula $(I)_{M6}$

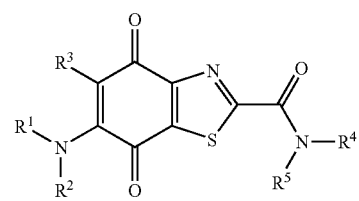

$(I)_{M6}$ in which $R^1$, $R^2$, $R^3$, $R^4$ and $R^5$ have the same meaning as in general sub-formula $(I)_M$.

According to another variant of the invention, the compounds of general formula (I) or their salts are such that $R^4$ represents a radical of formula

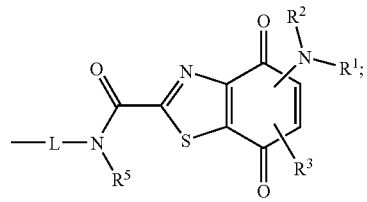

in the remainder of this disclosure, such compounds are called the "compounds of general sub-formula $(I)_D$".

Among the compounds of general sub-formula $(I)_D$, certain will correspond to general sub-formula $(I)_{D5}$

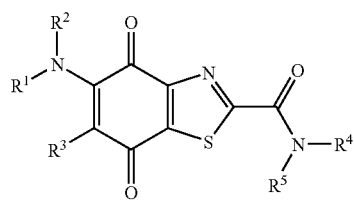

$(I)_{D5}$ in which $R^1$, $R^2$, $R^3$ and $R^5$ have the same meaning as in general sub-formula $(I)_D$ and $R^4$ represents a radical of formula

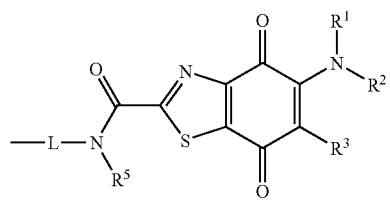

in which L has the same meaning as in general sub-formula $(I)_D$;

whilst the others will correspond to general sub-formula $(I)_{D6}$

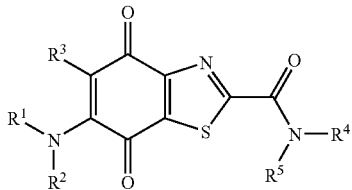

(I)$_{D6}$ in which R$^1$, R$^2$, R$^3$ and R$^5$ have the same meaning as in general sub-formula (I)$_D$ and R$^4$ represents a radical of formula

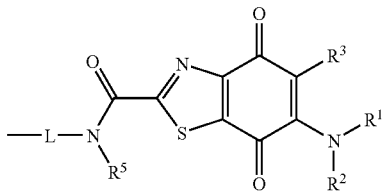

in which L has the same meaning as in general sub-formula (I)$_D$.

When the compounds of general sub-formula (I)$_D$ or their salts are such that L represents —(CH$_2$)$_a$-Ω-(CH$_2$)$_b$—, Ω is preferably —O—, —CO—, —CR$^{27}$R$^2$S— and more preferentially —O—.

Preferably, the compounds of general formula (I) or their salts are such that they possess independently at least one of the following characteristics:

R$^1$ represents an alkyl, cycloalkyl, alkoxyalkyl, —(CH$_2$)—X—Y, —(CH$_2$)—Z—NR$^6$R$^7$ or —CHR$^8$R$^9$ radical; or R$^2$ represents a hydrogen atom or the methyl, ethyl or benzyl radical; or R$^3$ represents a hydrogen atom; or R$^4$ represents an alkyl radical, a cycloalkyl radical, a cycloalkylalkyl radical, an alkoxyalkyl radical, one of the carbocyclic or heterocyclic aryl or carbocyclic or heterocyclic aralkyl radicals the aryl nucleus of which is optionally substituted 1 to 3 times by substituents chosen independently from the group constituted by a halogen atom, an alkyl radical, an alkoxy radical, a haloalkyl radical and an —SO$_2$—NH$_2$ radical, or also R$^4$ represents one of the —(CH$_2$)$_m$—[O—(CH$_2$)$_p$]$_q$—O-Alk, —(CH$_2$)$_r$—[O—(CH$_2$)$_s$]$_t$—NR$^{21}$R$^{22}$ or —(CH$_2$)$_v$-A radicals in which m, p and s are each independently 2 or 3, q is an integer from 1 to 3, t is an integer from 0 to 3, r is an integer from 2 to 6 and v is an integer from 1 to 6, Alk is an alkyl radical, R$^{21}$ is a hydrogen atom or an alkoxycarbonyl radical, R$^{22}$ is a hydrogen atom or a methyl radical and A is a saturated heterocycle containing 1 to 2 heteroatoms chosen independently from O, N and S and attached to the —(CH$_2$)$_v$— group by an N or CH member, said saturated heterocycle containing moreover 2 to 6 additional members chosen independently from —CHR$^{23}$—, —CO—, —NR$^{24}$—, —O— and —S—, R$^{23}$ representing a hydrogen atom or a methyl radical and R$^{24}$ representing a hydrogen atom, an alkyl radical or an alkoxycarbonyl group;

or also R$^4$ represents a radical of formula

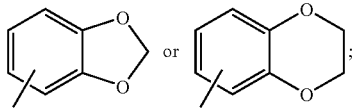

or

R$^5$ represents a hydrogen atom or an alkyl or aralkyl radical, R$^5$ also being able to represent a radical identical to R$^4$ when R$^4$ represents a carbocyclic alkyl, alkoxyalkyl or aralkyl radical the aryl nucleus of which is optionally substituted 1 to 3 times by substituents chosen independently from the group constituted by a halogen atom, an alkyl radical, an alkoxy radical, a haloalkyl radical and a —SO$_2$—NH$_2$ radical;

or also R$^4$ and R$^5$ form together with the nitrogen atom which carries them a saturated heterocycle with 4 to 7 members comprising 1 to 2 heteroatoms in total, the members necessary for completing the heterocycle being chosen independently from the —CH$_2$—, —O—, —S— and —NR$^{31}$— radicals, R$^{31}$ representing —COR$^{32}$— or —SO$_2$R$^{33}$—, R$^{32}$ representing an alkyl radical, a carbocyclic aryl radical optionally substituted 1 to 3 times by substituents chosen independently from the group constituted by a halogen atom, an alkyl radical and an alkoxy radical, or also R$^{32}$ representing a heterocyclic aryl radical or a saturated heterocycle chosen from the piperidino, piperazino, morpholino, thiomorpholino and 2-tetrahydrofuryl radicals, R$^{33}$ representing a hydrogen atom or an alkyl radical, or also R$^4$ and R$^5$ form together with the nitrogen atom which carries them a heterocyclic aryl radical of formula

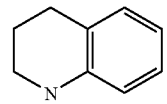

the aromatic ring of which can be substituted 1 to 3 times by an alkyl or alkoxy radical.

More preferentially, the compounds of general formula (I) or their salts are such that they possess independently at least one of the following characteristics:

R$^1$ represents a —(CH$_2$)—Z—NR$^6$R$^7$ radical,

Z representing a bond or a linear or branched alkylene radical containing 1 to 5 carbon atoms, R$^6$ and R$^7$ being chosen independently from a hydrogen atom and an alkyl radical, or also R$^6$ and R$^7$ forming together with the nitrogen atom a heterocycle with 4 to 7 members comprising 1 to 2 heteroatoms, the members necessary for completing the heterocycle being chosen independently from the —CH$_2$—, —O—, —S— and —NR$^{17}$— radicals, R$^{17}$ representing a hydrogen atom or an alkyl radical; or R$^2$ represents a hydrogen atom or the methyl radical; or R$^4$ represents an alkyl radical, a cycloalkyl radical, a cycloalkylalkyl radical, an alkoxyalkyl radical or a carbocyclic or heterocyclic aryl or carbocyclic or heterocyclic aralkyl radical the aryl nucleus of which is optionally substituted 1 to 3 times by substituents chosen independently from the group constituted by a halogen atom, an alkyl radical, an alkoxy radical, a haloalkyl radical and an —SO$_2$—NH$_2$ radical (and preferably chosen independently from the group constituted by a halogen atom, an alkyl radical and an alkoxy radical), or also R$^4$ represents one of the —(CH$_2$)$_m$—[O—(CH$_2$)$_p$]$_q$—O-Alk, —(CH$_2$)$_r$—[O—(CH$_2$)$_s$]$_t$—NR$^{21}$R$^{22}$ or —(CH$_2$)$_v$-A radicals in which m, p and s are each independently 2 or 3, q is an integer from 1 to 3, t is an integer from 0 to 3, r is an integer from 2 to 6 and v is an integer from 1 to 6, Alk is an alkyl radical, R$^{21}$ is a hydrogen atom or an alkoxycarbonyl radical, R$^{22}$ is a hydrogen atom or a methyl radical and A is a saturated heterocycle containing 1 to 2 heteroatoms chosen independently from O, N and S and attached to the —(CH$_2$)$_v$— group by an N or CH member, said saturated heterocycle moreover containing 2 to 6 additional members chosen independently from —CHR$^{23}$—, —CO—, —NR$^{24}$—, —O— and —S—, R$^{23}$ representing a hydrogen atom or a methyl radical and R$^{24}$ representing a hydrogen atom, an alkyl radical or an alkoxycarbonyl group;

or also R$^4$ represents a radical of formula

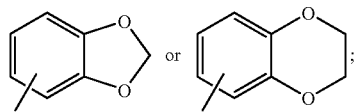

R$^5$ represents a hydrogen atom, R$^5$ also being able to represent a radical identical to R$^4$ when R$^4$ represents an carbocyclic alkyl, alkoxyalkyl or aralkyl radical the aryl nucleus of which is optionally substituted 1 to 3 times by substituents chosen independently from the group constituted by a halogen atom, an alkyl radical, an alkoxy radical, a haloalkyl radical and an —SO$_2$— NH$_2$ radical; or or also R$^4$ and R$^5$ form together with the nitrogen atom which carries them a saturated heterocycle with 4 to 7 members comprising 1 to 2 heteroatoms in total, the members necessary for completing the heterocycle being chosen independently from the —CH$_2$—, —O, —S— and —NR$^{31}$— radicals, R$^{31}$ representing —COR$^{32}$— or —SO$_2$R$^{33}$—, R$^{32}$ representing an alkyl radical, a carbocyclic aryl radical optionally substituted 1 to 3 times by substituents chosen independently from the group constituted by a halogen atom, an alkyl radical and an alkoxy radical, or also R32 representing a heterocyclic aryl radical chosen from the 2-furyl, 2-pyrrolyl and 2-thienyl radicals, or a saturated heterocycle chosen from the piperidino, piperazino, morpholino, thiomorpholino and 2-tetrahydrofuryl radicals, R$^{33}$ representing a hydrogen atom or a methyl radical, or also R$^4$ and R$^5$ form together with the nitrogen atom which carries them a heterocyclic aryl radical of formula

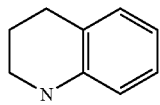

the aromatic ring of which can be substituted 1 to 3 times by an alkyl or alkoxy radical (and preferably by an alkoxy radical).

Still more preferentially, the compounds of general formula (I) or their salts are such that they possess independently at least one of the following characteristics:

R$^1$ representing a —(CH$_2$)—Z—NR$^6$R$^7$ radical,

Z representing a bond or a linear or branched alkylene radical containing 1 to 3 carbon atoms (and in particular 1 carbon atom), R$^6$ and R$^7$ being chosen independently from a hydrogen atom and an alkyl radical (and in particular R$^6$ and R$^7$ each representing a methyl radical), or also R$^6$ and R$^7$ forming together with the nitrogen atom a pyrrolidinyl or piperidinyl (and in particular pyrrolidinyl) ring;

R$^2$ representing a hydrogen atom;

R$^4$ representing an alkyl radical, a cycloalkyl radical, a cycloalkylalkyl radical, an alkoxyalkyl radical or a carbocyclic or heterocyclic aryl radical or a carbocyclic or heterocyclic aralkyl radical the aryl nucleus of which is optionally substituted 1 to 2 times by substituents chosen independently from the group constituted by a halogen atom, an alkyl radical or an alkoxy radical, or also R$^4$ representing one of the —(CH$_2$)$_m$—[O—(CH$_2$)$_p$]$_q$—O-Alk, —(CH$_2$)$_r$—[O—(CH$_2$)$_s$]$_t$—NR$^{21}$R$^{22}$ or —(CH$_2$)$_v$-A radicals in which m, p and s are each independently 2 or 3, q is an integer from 1 to 3, t is an integer from 0 to 3, r is an integer from 2 to 6 and v is an integer from 1 to 6, Alk is an alkyl radical containing 1 to 3 carbon atoms, R$^{21}$ is a hydrogen atom or an alkoxycarbonyl radical (and in particular tert-butoxycarbonyl), R$^{22}$ is a hydrogen atom and A is a saturated heterocycle containing 1 to 2 heteroatoms chosen independently from O, N and S and attached to the —(CH$_2$)$_v$— group by an N or CH member, said saturated heterocycle moreover containing 2 to 6 additional members chosen independently from —CH$_2$—, —CO—, —NR$^{24}$—, —O— an —S—, R$^{23}$ representing a hydrogen atom or a methyl radical and R$^{24}$ representing a hydrogen atom, an alkyl radical or an alkoxycarbonyl group;

or also R$^4$ represents a radical of formula

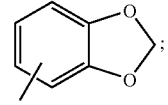

R$^5$ representing a hydrogen atom;

or also R$^4$ and R$^5$ forming together with the nitrogen atom which carries them a saturated heterocycle with 5 to 7 members comprising 1 to 2 heteroatoms in total, the members necessary for completing the heterocycle being chosen independently from the —CH$_2$—, —O—, —S— and —NR$^{31}$— radicals, R$^{31}$ representing —COR$^{32}$— or —SO$_2$R$^{33}$—, R$^{32}$ representing an alkyl radical, a carbocyclic aryl radical optionally substituted 1 to 3 times by substituents chosen independently from the group constituted by a halogen atom, an alkyl radical and an alkoxy radical, or also R$^{32}$ representing a heterocyclic aryl radical chosen from the 2-furyl, 2-pyrrolyl and 2-thienyl radicals, or a saturated heterocycle chosen from the piperidino, piperazino, morpholino, thiomorpholino and 2-tetrahydrofuryl radicals, $R^{33}$ representing an alkyl radical;

or also $R^4$ and $R^5$ form together with the nitrogen atom which carries them a heterocyclic aryl radical of formula

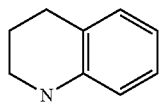

the aromatic ring of which can be substituted 1 to 3 times (and preferably once) by an alkoxy radical (and preferably by a methoxy radical).

More particularly the compounds of general formula (I) or their salts are such that they possess independently at least one of the following characteristics:

$R^1$ represents at least one radical chosen from the following radicals: $—(CH_2)_2—N(CH_3)_2$, or $—(CH_2)_2—O—CH_3$, or a

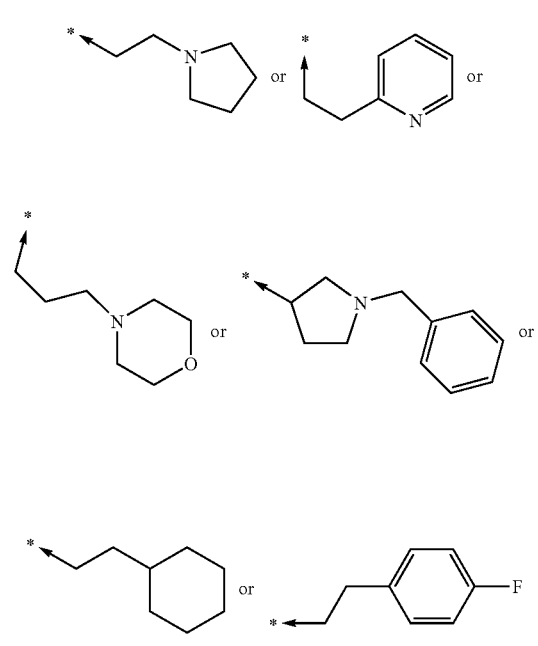

radical;

Or $R^1R^2N—$ represents a

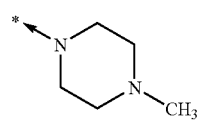

radical;

Or $R^2$ represents a hydrogen atom or a methyl radical;

Or $R^3$ represents a hydrogen or bromine atom;

Or $R^4$ represents at least one radical chosen from the following radicals:

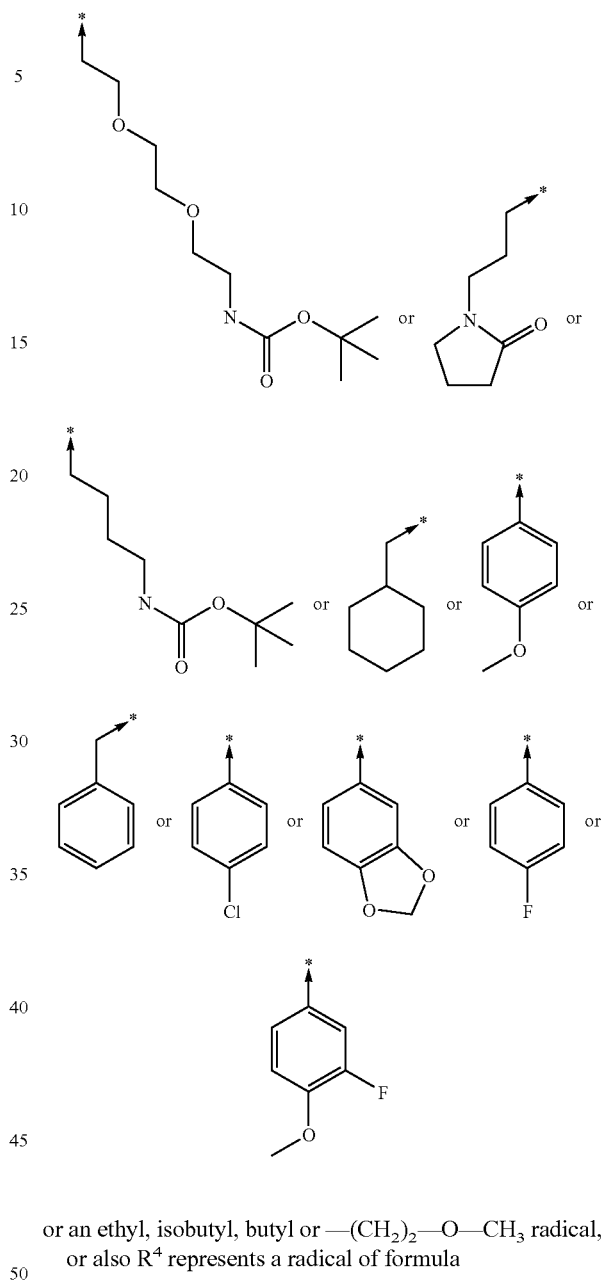

or an ethyl, isobutyl, butyl or $—(CH_2)_2—O—CH_3$ radical, or also $R^4$ represents a radical of formula

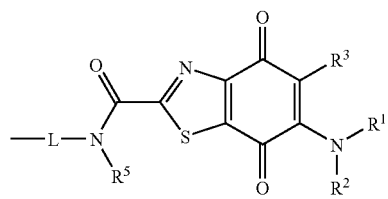

in which L represents a radical chosen independently from $—(CH_2)_2—O—(CH_2)_2—O—(CH_2)_2—$ or $—(CH_2)_2—O—(CH_2)_2—$, $R^5$, $R^3$ and $R^2$ represent H and R1 represents $—(CH_2)_2—N(CH_3)_2$;

Or $R^5$ represents a hydrogen atom or a $—(CH_2)_2—O—CH_3$ radical or a

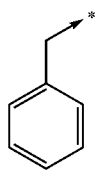

radical;

or also R⁴ and R⁵ forming together with the nitrogen atom which carries them a heterocycle chosen from the following heterocycles:

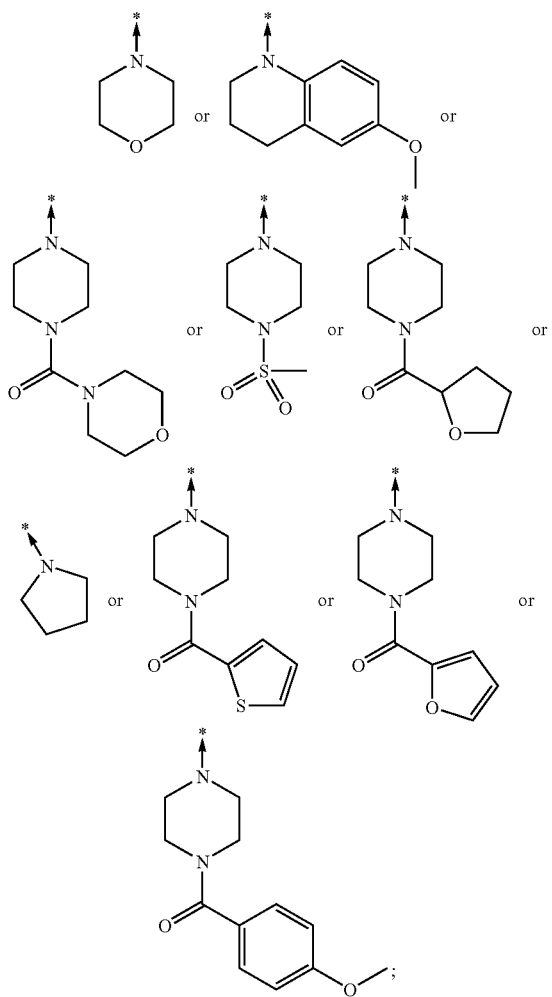

it being understood that ➔ * signifies the attachment point to general formula (I).

Among the compounds of general formula (I), the following compounds described in the examples will be preferred in particular:

5-{[2-(dimethylamino)ethyl]amino}-2-(morpholin-4-ylcarbonyl)-1,3-benzothiazole-4,7-dione;
tert-butyl{2-[2-(2-{[(5-{[2-(dimethylamino)ethyl]amino}-4,7-dioxo-4,7-dihydro-1,3-benzothiazol-2-yl)carbonyl]amino}ethoxy)ethoxy]ethyl}carbamate;
N,N-dibenzyl-5-{[2-(dimethylamino)ethyl]amino}-4,7-dioxo-4,7-dihydro-1,3-benzothiazole-2-carboxamide;
5-{[2-(dimethylamino)ethyl]amino}-N,N-bis(2-methoxyethyl)-4,7-dioxo-4,7-dihydro-1,3-benzothiazole-2-carboxamide;
5-{[2-(dimethylamino)ethyl]amino}-4,7-dioxo-N-[3-(2-oxopyrrolidin-1-yl)propyl]-4,7-dihydro-1,3-benzothiazole-2-carboxamide;
4,7-dioxo-N-[3-(2-oxopyrrolidin-1-yl)propyl]-5-[(2-pyrrolidin-1-ylethyl)amino]-4,7-dihydro-1,3-benzothiazole-2-carboxamide;
5-{[2-(dimethylamino)ethyl]amino}-N-isobutyl-4,7-dioxo-4,7-dihydro-1,3-benzothiazole-2-carboxamide;
tert-butyl (4-{[(5-{[2-(dimethylamino)ethyl]amino}-4,7-dioxo-4,7-dihydro-1,3-benzothiazol-2-yl)carbonyl]amino}butyl)carbamate;
5-{[2-(dimethylamino)ethyl]amino}-2-{[4-(2-furoyl)piperazin-1-yl]carbonyl}-1,3-benzothiazole-4,7-dione;
5-{[2-(dimethylamino)ethyl]amino}-N-(2-methoxyethyl)-4,7-dioxo-4,7-dihydro-1,3-benzothiazole-2-carboxamide;
N-butyl-5-{[2-(dimethylamino)ethyl]amino}-4,7-dioxo-4,7-dihydro-1,3-benzothiazole-2-carboxamide;
N-benzyl-5-{[2-(dimethylamino)ethyl]amino}-4,7-dioxo-4,7-dihydro-1,3-benzothiazole-2-carboxamide;
N-(cyclohexylmethyl)-5-{[2-(dimethylamino)ethyl]amino}-4,7-dioxo-4,7-dihydro-1,3-benzothiazole-2-carboxamide;
N,N'-(oxydiethane-2,1-diyl)bis(5-{[2-(dimethylamino)ethyl]amino}-4,7-dioxo-4,7-dihydro-1,3-benzothiazole-2-carboxamide);
N,N'-[ethane-1,2-diylbis(oxyethane-2,1-diyl)]bis(5-{[2-(dimethylamino)ethyl]amino}-4,7-dioxo-4,7-dihydro-1,3-benzothiazole-2-carboxamide);
5-{[2-(dimethylamino)ethyl]amino}-2-{[4-(morpholin-4-ylcarbonyl)piperazin-1-yl]carbonyl}-1,3-benzothiazole-4,7-dione;
2-{[4-(morpholin-4-ylcarbonyl)piperazin-1-yl]carbonyl}-5-[(2-pyrrolidin-1-ylethyl)amino]-1,3-benzothiazole-4,7-dione;
5-{[2-(dimethylamino)ethyl]amino}-N-(4-methoxyphenyl)-4,7-dioxo-4,7-dihydro-1,3-benzothiazole-2-carboxamide;
5-{[2-(dimethylamino)ethyl]amino}-2-{[4-(methylsulphonyl)piperazin-1-yl]carbonyl}-1,3-benzothiazole-4,7-dione;
5-{[2-(dimethylamino)ethyl]amino}-2-{[4-(tetrahydrofuran-2-ylcarbonyl)piperazin-1-yl]carbonyl}-1,3-benzothiazole-4,7-dione;
6-bromo-5-{[2-(dimethylamino)ethyl]amino}-2-{[4-(tetrahydrofuran-2-ylcarbonyl)piperazin-1-yl]carbonyl}-1,3-benzothiazole-4,7-dione;
5-{[2-(dimethylamino)ethyl]amino}-2-(pyrrolidin-1-ylcarbonyl)-1,3-benzothiazole-4,7-dione;
5-{[2-(dimethylamino)ethyl]amino}-2-{[4-(2-thienylcarbonyl)piperazin-1-yl]carbonyl}-1,3-benzothiazole-4,7-dione;
5-{[2-(dimethylamino)ethyl]amino}-N-ethyl-4,7-dioxo-4,7-dihydro-1,3-benzothiazole-2-carboxamide;
N-(4-chlorophenyl)-5-{[2-(dimethylamino)ethyl]amino}-4,7-dioxo-4,7-dihydro-1,3-benzothiazole-2-carboxamide;
N-1,3-benzodioxol-5-yl-5-{[2-(dimethylamino)ethyl]amino}-4,7-dioxo-4,7-dihydro-1,3-benzothiazole-2-carboxamtide;
5-[(2-methoxyethyl)amino]-2-{[4-(tetrahydrofuran-2-ylcarbonyl)piperazin-1-yl]carbonyl}-1,3-benzothiazole-4,7-dione;
5-(4-methylpiperazin-1-yl)-2-{[4-(tetrahydrofuran-2-ylcarbonyl)piperazin-1-yl]carbonyl}-1,3-benzothiazole-4,7-dione;

5-[(2-pyridin-2-ylethyl)amino]-2-{[4-(tetrahydrofuran-2-yl-carbonyl)piperazin-1-yl]carbonyl}-1,3-benzothiazole-4,7-dione;

5-[(3-morpholin-4-ylpropyl)amino]-2-{[4-(tetrahydrofuran-2-ylcarbonyl)piperazin-1-yl]carbonyl}-1,3-benzothiazole-4,7-dione;

5-[(1-benzylpyrrolidin-3-yl)amino]-2-{[4-(tetrahydrofuran-2-ylcarbonyl)piperazin-1-yl]carbonyl}-1,3-benzothiazole-4,7-dione;

5-[(2-cyclohexylethyl)amino]-2-{[4-(tetrahydrofuran-2-yl-carbonyl)piperazin-1-yl]carbonyl}-1,3-benzothiazole-4,7-dione;

5-{[2-(dimethylamino)ethyl]amino}-N-(4-fluorophenyl)-4,7-dioxo-4,7-dihydro-1,3-benzothiazole-2-carboxamide;

6-{[2-(dimethylamino)ethyl]amino}-2-(pyrrolidin-1-ylcarbonyl)-1,3-benzothiazole-4,7-dione;

5-{[2-(dimethylamino)ethyl]amino}-N-(3-fluoro-4-methoxyphenyl)-4,7-dioxo-4,7-dihydro-1,3-benzothiazole-2-carboxamide;

5-{[2-(dimethylamino)ethyl]amino}-2-[(6-methoxy-3,4-dihydroquinolin-1(2H)-yl)carbonyl]-1,3-benzothiazole-4,7-dione;

5-{[2-(dimethylamino)ethyl]amino}-2-{[4-(4-methoxybenzoyl)piperazin-1-yl]carbonyl}-1,3-benzothiazole-4,7-dione;

5-[[2-(dimethylamino)ethyl](methyl)amino]-N-ethyl-4,7-dioxo-4,7-dihydro-1,3-benzothiazole-2-carboxamide;

N-ethyl-5-{[2-(4-fluorophenyl)ethyl]amino}-4,7-dioxo-4,7-dihydro-1,3-benzothiazole-2-carboxamide;

and the salts of these compounds.

The following compounds are more particularly preferred:

5-{[2-(dimethylamino)ethyl]amino}-2-(morpholin-4-ylcarbonyl)-1,3-benzothiazole-4,7-dione;

5-{[2-(dimethylamino)ethyl]amino}-4,7-dioxo-N-[3-(2-oxopyrrolidin-1-yl)propyl]-4,7-dihydro-1,3-benzothiazole-2-carboxamide;

5-{[2-(dimethylamino)ethyl]amino}-2-{[4-(2-furoyl)piperazin-1-yl]carbonyl}-1,3-benzothiazole-4,7-dione;

5-{[2-(dimethylamino)ethyl]amino}-N-(4-methoxyphenyl)-4,7-dioxo-4,7-dihydro-1,3-benzothiazole-2-carboxamide;

5-{[2-(dimethylamino)ethyl]amino}-2-(pyrrolidin-1-ylcarbonyl)-1,3-benzothiazole-4,7-dione;

5-{[2-(dimethylamino)ethyl]amino}-2-{[4-(2-thienylcarbonyl)piperazin-1-yl]carbonyl}-1,3-benzothiazole-4,7-dione;

N-1,3-benzodioxol-5-yl-5-{[2-(dimethylamino)ethyl]amino}-4,7-dioxo-4,7-dihydro-1,3-benzothiazole-2-carboxamide;

5-{[2-(dimethylamino)ethyl]amino}-N-(4-fluorophenyl)-4,7-dioxo-4,7-dihydro-1,3-benzothiazole-2-carboxamide;

6-{[2-(dimethylamino)ethyl]amino}-2-(pyrrolidin-1-ylcarbonyl)-1,3-benzothiazole-4,7-dione;

5-{[2-(dimethylamino)ethyl]amino}-N-(3-fluoro-4-methoxyphenyl)-4,7-dioxo-4,7-dihydro-1,3-benzothiazole-2-carboxamide;

5-{[2-(dimethylamino)ethyl]amino}-2-[(6-methoxy-3,4-dihydroquinolin-1(2H)-yl)carbonyl]-1,3-benzothiazole-4,7-dione;

5-{[2-(dimethylamino)ethyl]amino}-2-{[4-(4-methoxybenzoyl)piperazin-1-yl]carbonyl}-1,3-benzothiazole-4,7-dione;

and the salts of these compounds.

The invention also relates, as medicaments, to the compounds of general formula (I) mentioned above, or their pharmaceutically acceptable salts.

A subject of the invention is also the pharmaceutical compositions comprising, as active ingredient, a compound of general formula (I) or a pharmaceutically acceptable salt of such a compound, with at least one pharmaceutically acceptable excipient.

Another subject of the invention is the use of the compounds of general formula (I) or of their pharmaceutically acceptable salts for preparing a medicament intended to treat a disease or a disorder chosen from the following diseases or the following disorders: tumorous proliferative diseases (and in particular cancer), non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases or allergies.

Quite particularly, the compounds of general formula (I) or their pharmaceutically acceptable salts can be used for preparing a medicament intended to treat cancer, and in particular breast cancer, lymphomas, cancers of the neck or head, lung cancer, cancer of the colon, cancer of the prostate or cancer of the pancreas.

The invention relates moreover to a treatment method for one of the diseases/one of the disorders mentioned, said method comprising the administration to the patient suffering from said disease/said disorder of a therapeutically effective quantity of a compound of general formula (I) or of a pharmaceutically acceptable salt of such a compound.

The invention also offers, as novel industrial products, the intermediates of general formula (A)

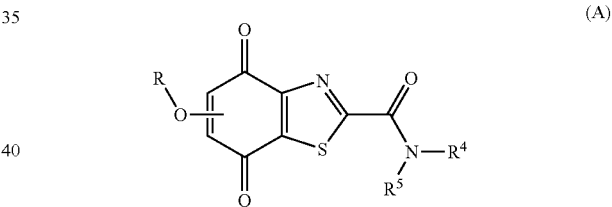

(A)

in which R is an alkyl radical, $R^5$ has the same meaning as in general formula (I)

and $R^4$ represents an alkyl radical, a haloalkyl radical, a cycloalkyl radical, a cycloalkylalkyl radical, an alkoxyalkyl radical, one of the carbocyclic or heterocyclic aryl or carbocyclic or heterocyclic aralkyl radicals the aryl nucleus of which is optionally substituted 1 to 3 times by substituents chosen independently from the group constituted by a halogen atom, an alkyl radical, an alkoxy radical, a haloalkyl radical and an —$SO_2$—$NH_2$ radical, or also $R^4$ represents one of the —$(CH_2)_m$—[O—$(CH_2)_p$]$_q$—O-Alk, —$(CH_2)_r$—[O—$(CH_2)_s$]$_t$—$NR^{21}R^{22}$ or —$(CH_2)_v$-A radicals in which m, p and s are each independently an integer from 2 to 4, q is an integer from 1 to 4, t is an integer from 0 to 4, r is an integer from 2 to 12 (and preferably an integer from 2 to 8 and in particular an integer from 2 to 6) and v is an integer from 1 to 12 (and preferably an integer from 1 to 8 and in particular an integer from 1 to 6), Alk is an alkyl radical, $R^{21}$ is a hydrogen atom or an alkyl, alkoxycarbonyl or aralkoxycarbony radical, $R^{22}$ is a hydrogen atom or an alkyl radical and A is a saturated heterocycle containing 1 to 2 heteroatoms chosen independently from O, N and S and attached to the —(CH$_2$)$_v$— group by an N or CH member, said saturated heterocycle moreover containing 2 to 6 additional members chosen independently from —CHR$^{23}$—, —CO—, —NR$^{24}$—, —O— and —S—, R$^{23}$ representing a hydrogen atom or an alkyl radical and R$^{24}$ representing a hydrogen atom, an alkyl radical or an alkoxy carbonyl or aralkoxycarbonyl group, or also R$^4$ represents a radical of formula

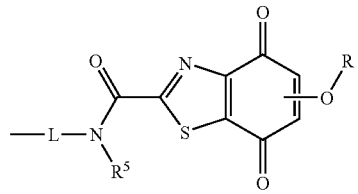

in which R and R$^5$ are identical to the R and R$^5$ radicals mentioned previously and L is chosen from the —(CH$_2$)$_g$—[O—(CH$_2$)$_w$]$_x$—[O—(CH$_2$)$_y$]$_z$— and —(CH$_2$)$_a$-Ω-(CH$_2$)$_b$— radicals in which g, w and y are integers from 2 to 4 (and preferably 2 to 3), x is an integer from 1 to 3 and z is 0 or 1, a and b are independently integers from 2 to 6 (and preferably 2 to 4) and Ω is chosen from the group constituted by —O—, —S—, —NR$^{25}$—, —CO—, —CO—NR$^{26}$—, —CR$^{27}$R$^{28}$—, a cycloalkylene radical containing 3 to 7 carbon atoms and finally a carbocyclic aryl radical, R$^{25}$ representing an alkyl radical, R$^{26}$ representing a hydrogen atom or a methyl radical, R$^{27}$ and R$^{28}$ each being chosen independently from a hydrogen atom and a methyl group;

or also R$^4$ represents a radical of formula

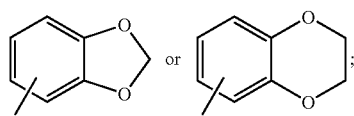

and the salts of such compounds.

According to a variant of the invention, said compounds of general formula (A) are such that R$^4$ does not represent a radical of formula

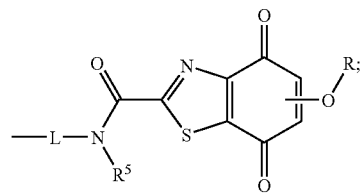

in the remainder of this disclosure, such compounds are called "compounds of general sub-formula (A)$_M$".

A particular feature of this variant of the invention relates to the compounds of general sub-formula (A)$_{M5}$

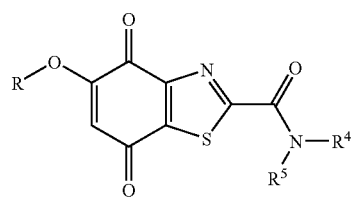

in which R, R$^4$ and R$^5$ have the same meaning as in general formula (A).

Another feature of this variant of the invention relates to the compounds of general sub-formula (A)$_{M6}$

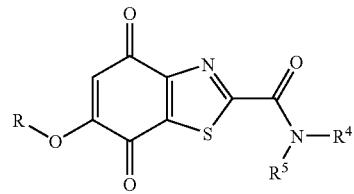

in which R, R$^4$ and R$^5$ have the same meaning as in general formula (A).

According to another variant of the invention, said compounds of general formula (A) are such that R$^4$ represents a radical of formula

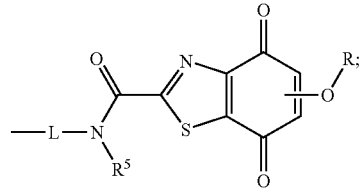

in the remainder of this disclosure, such compounds are called the "compounds of general sub-formula (A)$_D$".

A particular feature of this variant of the invention relates to the compounds of general sub-formula (A)$_{D5}$

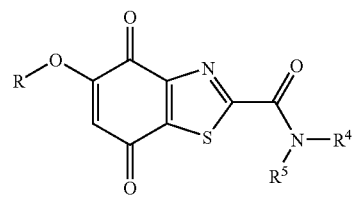

in which R and R$^5$ have the same meaning as in general formula (A) whilst R$^4$ represents a radical of formula

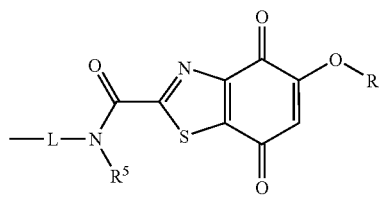

in which L, R and R⁵ have the same meaning as in general formula (A).

Another feature of this variant of the invention relates to the compounds of general sub-formula (A)$_{D6}$

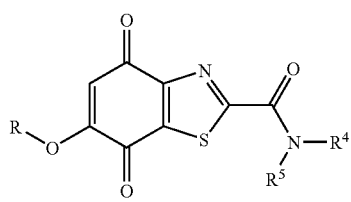

in which R and R⁵ have the same meaning as in general formula (A) whilst R⁴ represents a radical of formula

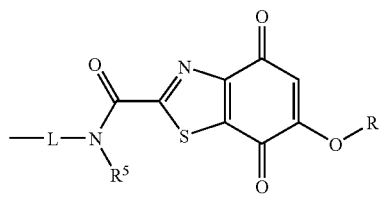

in which L, R and R⁵ have the same meaning as in general formula (A).

The preferences indicated for the compounds of general formulae (I), (I)$_M$ or (I)$_D$ or their salts are applicable *mutatis mutandis* to these compounds or their pharmaceutically acceptable salts as medicaments, to the pharmaceutical compositions containing these compounds or their pharmaceutically acceptable salts, to the uses of these compounds or of their pharmaceutically acceptable salts, to the treatment methods according to the invention or to the intermediates of general formulae (I), (A)$_M$ or (A)$_D$ or their salts.

The pharmaceutical compositions containing a compound of the invention can be presented in the solid form, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, the water, organic solvents such as glycerol or the glycols, as well as their mixtures, in varying proportions, in water.

The administration of a medicament according to the invention can be carried out by topical, oral, parenteral route, by intramuscular injection, etc.

The administration dose envisaged for a medicament according to the invention is comprised between 0.1 mg to 10 g depending on the type of active ingredient used.

According to the invention, the compounds of general formula (I) can be prepared by the processes described hereafter.

Preparation of the Compounds of General Formula (I)

A distinction is to be made between two cases, according to whether the compounds of general sub-formula (I)$_M$ or those of general sub-formula (I)$_D$ are concerned.

Of course, the preparation processes hereafter are given by way of illustration and a person skilled in the art can subject them to the variations deemed useful, both with respect to the reagents and to the reaction conditions and techniques.

General Method:

The compounds of general formula (I)$_M$ in which R³ represents a hydrogen atom can be prepared according to the procedure summarized in Diagram 1 hereafter.

Diagram 1

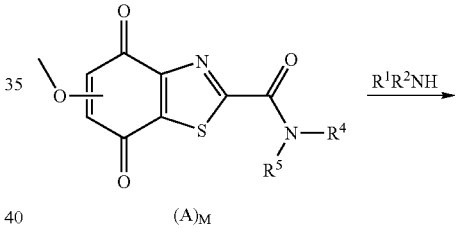

(A)$_M$

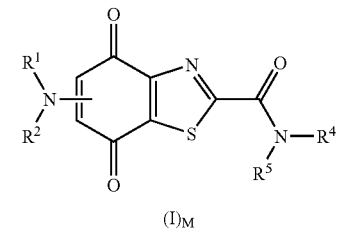

(I)$_M$

According to this method, the compounds of general formula (I)$_M$, in which R¹, R², R⁴ and R⁵ are as described above, are obtained by treatment of the compounds of general formula (A)$_M$, in which R⁴ and R⁵ have the same meaning as in general formula (I)$_M$, with the amines of general formula R¹R²NH in a protic solvent such as methanol or ethanol, at a temperature comprised between 20° C. and 80° C. and optionally in the presence of a base such as, for example, diisopropylethylamine (cf. Yasuyuki Kita et al., *J. Org. Chem.* (1996), 61, 223-227).

The compounds of general formula (I)$_D$ in which R³ represents a hydrogen atom can be prepared according to the procedure summarized in Diagram 1a hereafter.

Diagram 1a

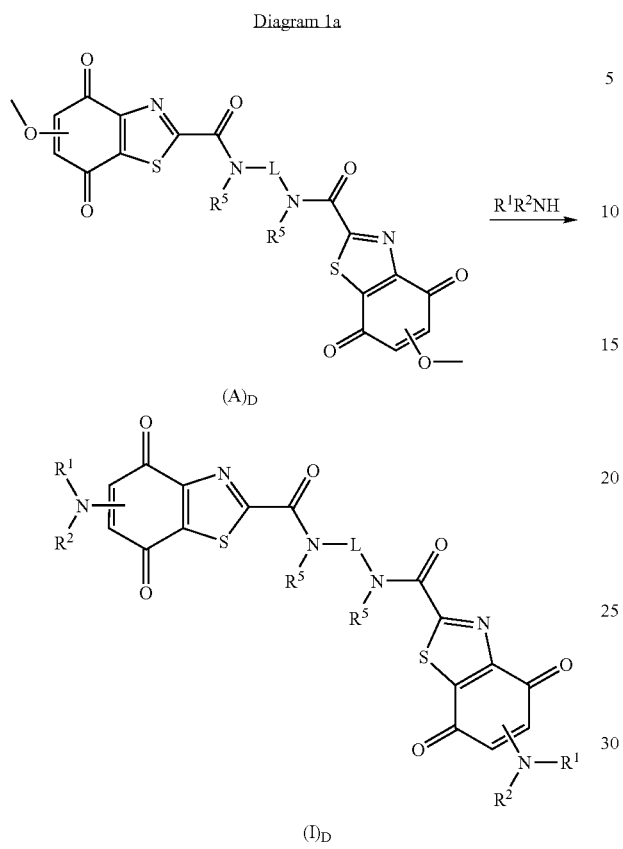

Renault et al., *J. Med. Chem.* (1983), 26, 1715-1719). (cf. Diagram 1b where only the compounds of general sub-formula $(I)_M$ are represented).

Diagram 1b

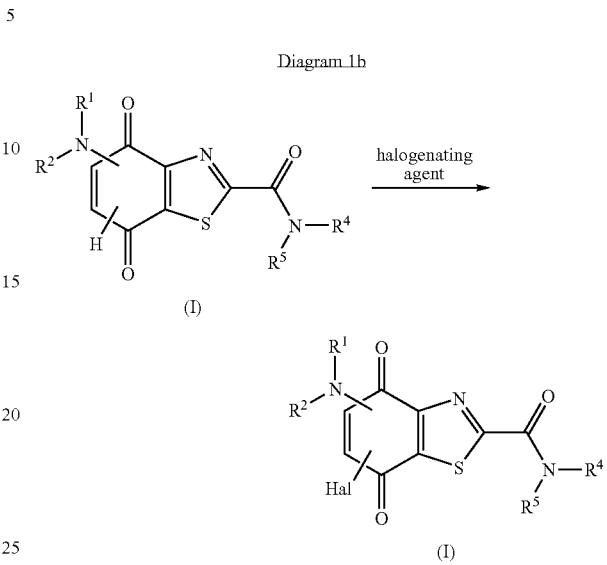

According to this method, the compounds of general sub-formula $(I)_D$, in which $R^1$, $R^2$, L and $R^5$ are as described above, are obtained by treatment of the compounds of general formula $(A)_D$, in which L and $R^5$ have the same meaning as in general sub-formula $(I)_D$, with the amines of general formula $R^1R^2NH$ in a protic solvent such as methanol or ethanol, at a temperature comprised between 20° C. and 80° C. and optionally in the presence of a base such as, for example, diisopropylethylamine (cf. Yasuyuki Kita et al., *J. Org. Chem.* (1996), 61, 223-227).

Generally, the compounds of general sub-formulae $(I)_M$ or $(I)_D$ in which $R^3$ represents a halogen atom (Hal) can be obtained from the correspondent compounds of general sub-formulae $(I)_M$ or $(I)_D$ in which $R^3$ represents a hydrogen atom, for example by the action of N-chlorosuccinimide or N-bromosuccinimide in an aprotic solvent such as dichloromethane or tetrahydrofuran (Paquette and Farley, *J. Org. Chem.* (1967), 32, 2725-2731), by the action of an aqueous solution of sodium hypochlorite (Javel water) in a solvent such as acetic acid (Jagadeesh et al., *Synth Commun.* (1998), 28, 3827-3833), by the action of Cu(II) (in a $CuCl_2/HgCl_2$ mixture) in the presence of a catalytic quantity of iodine in a solvent such as warm acetic acid (Thapliyal, *Synth. Commun.* (1998), 28, 1123-1126), by the action of an agent such as benzyltrimethylammonium dichloroiodate in the presence of $NaHCO_3$ in a solvent such as a dichloromethane/methanol mixture (Kordik and Reitz, *J. Org. Chem.* (1996), 61, 5644-5645), or also by the use of chlorine, bromine or iodine in a solvent such as dichloromethane (J. Renault, S. Giorgi- Preparation of the Intermediates of General Formula $(A)_M$ and $(A)_D$ The compounds of general sub-formula $(A)_M$, in which $R^4$ and $R^5$ are as defined above, can be obtained, Diagram 2, from the compounds of general formula $(B)_M$ in which $R^4$ and $R^5$ are as defined above and one of Q and Q' represents an amino radical whilst the other represents a hydrogen atom.

Diagram 2

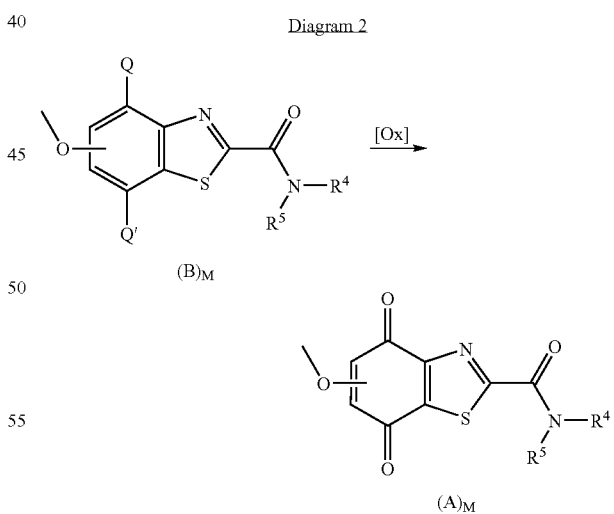

In the same way, the compounds of general formula $(A)_D$, in which L and $R^5$ are as defined above, can be obtained, Diagram 2a, from the compounds of general formula $(B)_D$ in which L and $R^5$ are as defined above and one of Q and Q' represents an amino radical whilst the other represents a hydrogen atom.

Diagram 2a

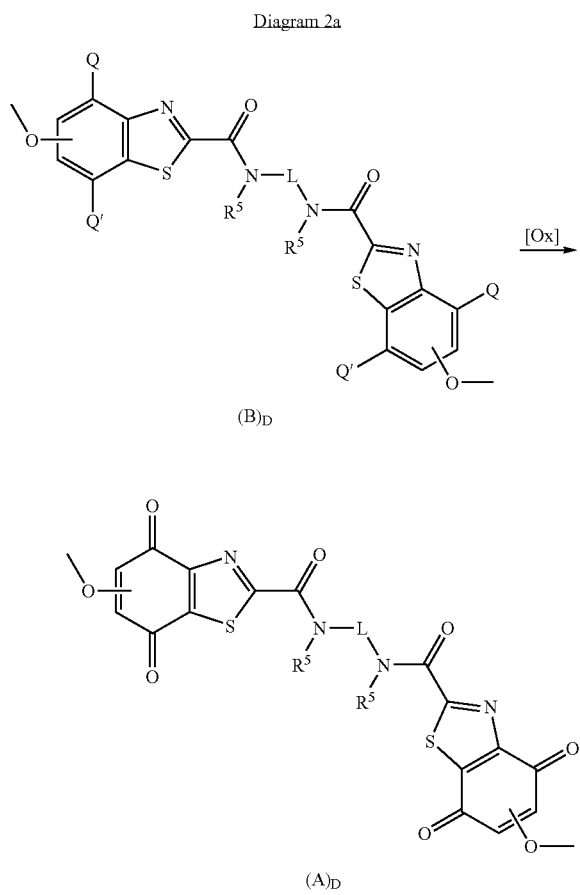

$(B)_D$ $(A)_D$

The compounds of general formula $(A)_M$ or $(A)_D$ are obtained by oxidation of the compounds of general formula $(B)_M$ or $(B)_D$ respectively, for example by the use of an ion exchange resin of Dowex type in the form of hypochlorite in anhydrous medium (Hashemi et al., *J. Chem. Res., Synop.* (1999), 11, 672-673) or Fremy's salt (potassium nitrosodisulphonate) (Ryu et al., *Bioorg. Med. Chem. Lett.* (2000), 10, 461-464), or by the use of a reagent comprising a hypervalent iodine such as [bis(acetoxy)iodo]benzene or [bis(trifluoroacetoxy)iodo]benzene in aqueous acetonitrile at a temperature preferably comprised between −20° C. and ambient temperature (i.e. approximately 25° C.), and preferably at approximately −5° C. (Kinugawa et al., *Synthesis*, (1996), 5, 633-636).

Preparation of the Intermediates of General Formula $(B)_M$ and $(B)_D$

The compounds of general formula $(B)_M$, in which Q, Q', $R^4$ and $R^5$ are as defined above, can be obtained from the nitro derivatives of formula $(C)_M$ in which $R^4$ and $R^5$ are as defined above and one of Q and Q' represents a nitro radical whilst the other is a hydrogen atom, by reduction methods well known to a person skilled in the art such as, for example, hydrogenation in the presence of a palladinized catalyst or treatment by tin chloride in hydrochloric acid.

The preparation of the compounds of general formula $(B)_M$ in which the methoxy group is in position 5 is represented in Diagram 3 below for the case where, for example, $Q=NH_2$ and $Q'=H$.

Diagram 3

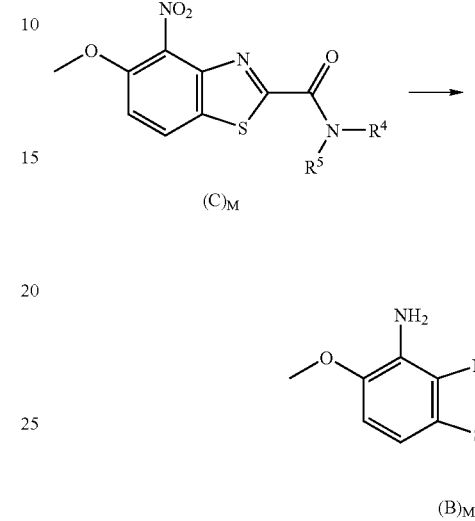

$(C)_M$ $(B)_M$

The preparation of the compounds of general formula $(B)_M$ in which the methoxy group is in position 6 is represented in Diagram 3a below for the case where, for example, Q=H and $Q'=NH_2$.

Diagram 3a

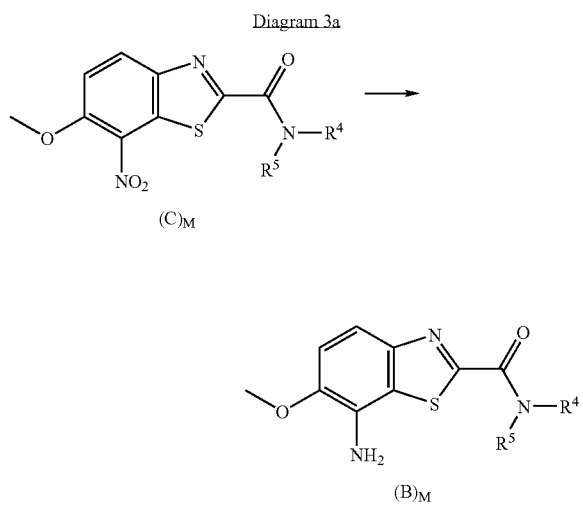

$(C)_M$ $(B)_M$

In the same way, the compounds of general formula $(B)_D$, in which Q, Q', L and $R^5$ are as defined above, can be obtained from the nitro derivatives of formula $(C)_D$ in which L and $R^5$ are as defined above and one of Q and Q' represents a nitro radical whilst the other represents a hydrogen atom (see Diagrams 3b and 3c below).

Diagram 3a

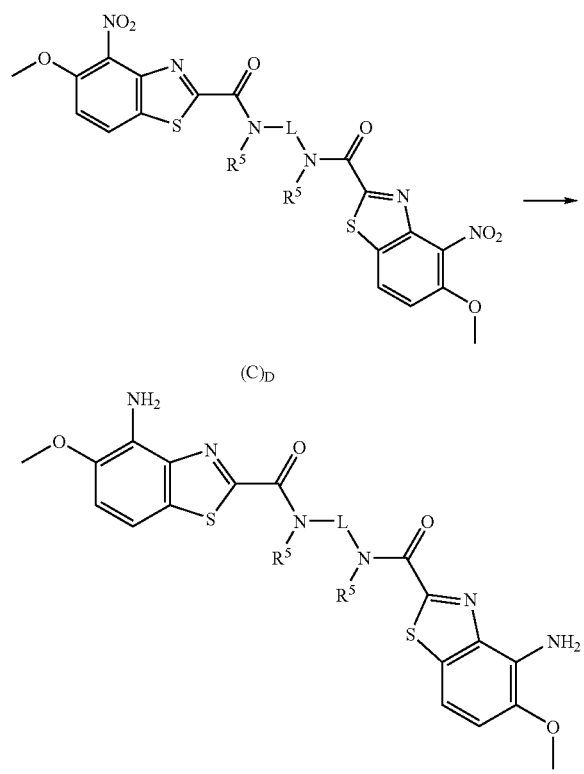

Diagram 3b

Preparation of the Intermediates of General Formula $(C)_M$ and $(C)_D$

The compounds of general formula (C)M in which $R^4$ and $R^5$ are as defined above and one of Q and Q' represents a nitro radical whilst the other represents a hydrogen atom, can be obtained, Diagram 4, from the compounds of general formula (D), in which Q and Q' are as defined above, and the amines of general formula $R^4R^5NH$.

Diagram 4

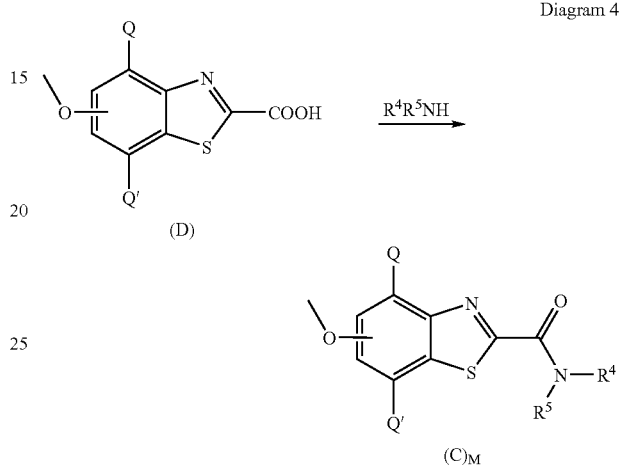

In the same way, the compounds of general formula $(C)_D$ in which L and $R^5$ are as defined above and one of Q and Q' represents a nitro radical whilst the other represents a hydrogen atom, can be obtained, Diagram 4a, from the compounds of general formula (D), in which Q and Q' are as defined above, and the diamines of general formula $R^5HN\text{-}L\text{-}NHR^5$.

Diagram 4a

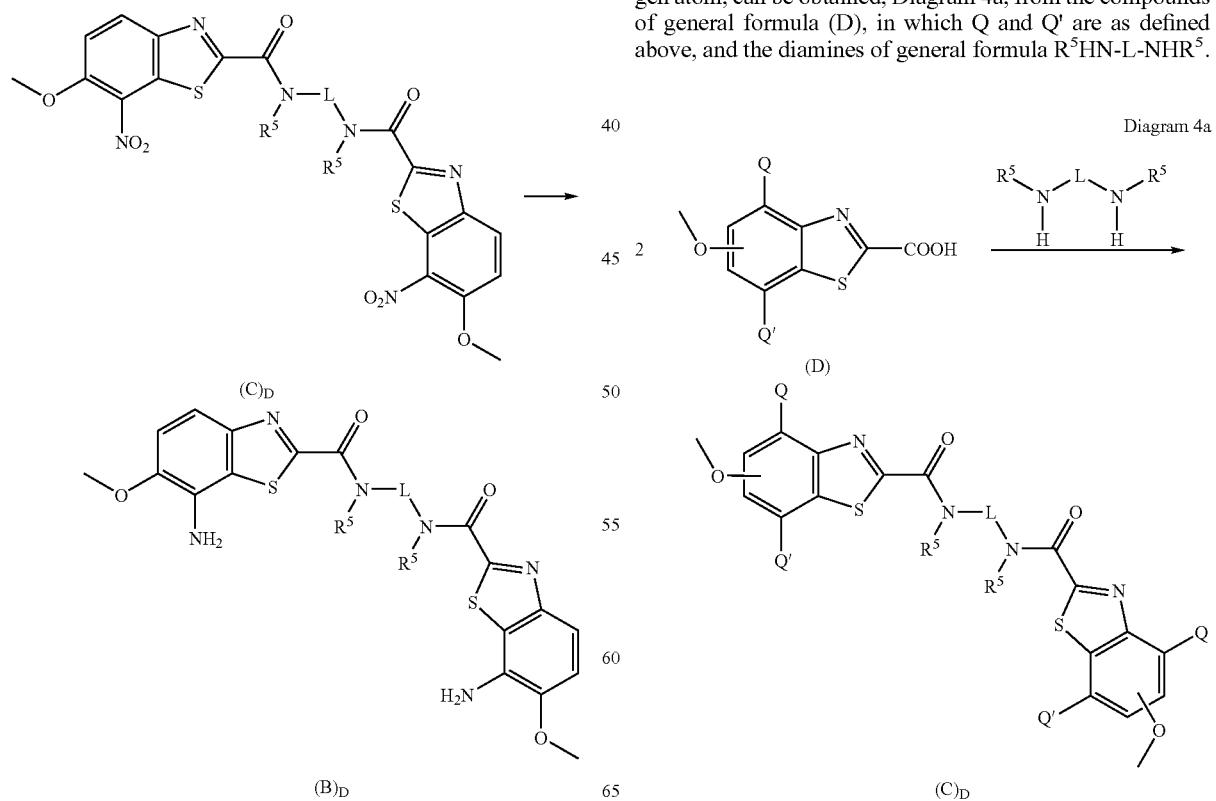

The compounds of general formula $(C)_M$ or $(C)_D$ are obtained as indicated above using the standard conditions for peptide synthesis (M. Bodansky, The Practice of Peptide Synthesis, 145 (Springer-Verlag, 1984)), for example in dichloromethane in the presence of a coupling reagent such as bromo-tris-pyrrolidino-phosphonium hexafluorophosphate (PyBroP) in the presence of dimethylaminopyridine (DMAP) (Coste et al., *Tetrahedron Lett.* (1990), 31, 669), or in a mixture (dimethylformamide/dichloromethane/dioxane: 1/1/1) in the presence of 1-(3-dimethylaminopropyl)-3-ethylcarbodiimide hydrochloride, a catalytic quantity of dimethylaminopyridine and diisopropylethylamine, or also by the formation of an intermediate acid chloride obtained by the addition of oxalyl chloride in solution to dichloromethane.

Preparation of the Intermediates of General Formula (D)

The compounds of general formula (D), in which Q and Q' are as defined above, can be obtained, Diagram 5, by oxidation of the carboxaldehydes of general formula (E.i) by the action of a oxidizing agent such as, for example sodium chlorite in a buffered solution of sodium hydrogen phosphate (pH 3.5) and in an aqueous solution of tert-butanol in the presence of 2-methyl-2-butene; these aldehydes of general formula (E.i) themselves being obtained by oxidation of the compounds of general formula (E) by the action, for example, of selenium oxide in 1,4-dioxane at 80° C. (Bu et al., *J. Med. Chem.* (2001), 44, 2004-2014).

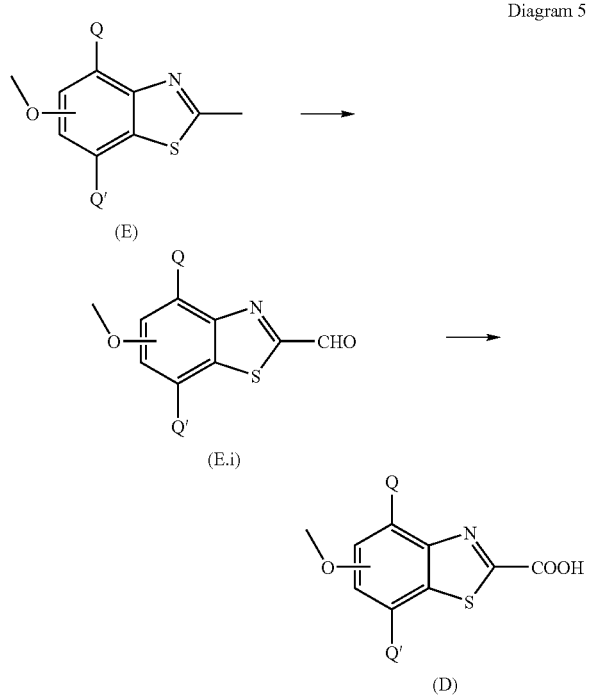

Preparation of the Intermediates of General Formula (E)

The compounds of general formula (E), in which Q and Q' are as defined above, can be obtained from the compounds of general formula (F), in which the positions corresponding to the Q and Q' radicals are substituted by hydrogen atoms, by nitration methods well known to a person skilled in the art such as, for example, treatment by a mixture of nitric acid and sulphuric acid.

The preparation of the compounds of general formula (E) in which the methoxy group is in position 5 is represented in Diagram 6 below for the case where, for example, $Q=NO_2$ and $Q'=H$.

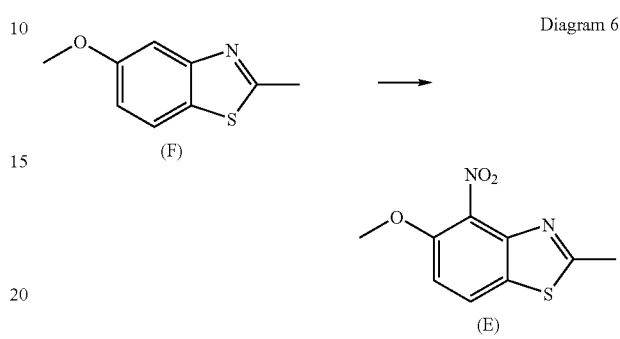

The preparation of the compounds of general formula (E) in which the methoxy group is in position 6 is represented in Diagram 6a below for the case where, for example, $Q=H$ and $Q'=NO_2$.

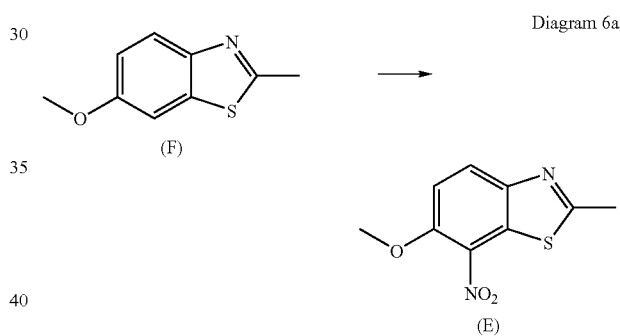

Compounds of General Formula (F)

The compounds of general formula (F) are known industrial products available from the usual suppliers or can be synthesized from such products according to methods familiar to a person skilled in the art.

As regards the temperatures to which reference is made in the present text, the term "approximately XX° C." indicates that the temperature in question corresponds to an interval within 10° C. above or below the temperature of XX° C., and preferably to an interval within 5° C. above or below the temperature of XX° C.

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as limiting the scope of the invention.

The melting points were measured using a Büchi 535 capillary apparatus.

The NMR spectra were recorded using a Brücker ARX 400 spectrometer. The chemical shifts are expressed in parts per million (ppm) with respect to tetramethylsilane (TMS) and the multiplicity of the signals is given in the form of s (singlet), d (doublet), t (triplet), m (multiplet).

EXAMPLES

Method Used for Measuring the Retention Time (r.t.) and of the Molecular Peak (MH+)

The compounds are characterized by their retention time (r.t.), expressed in minutes, determined by liquid chromatography (LC), and their molecular peak (MH+) determined by mass spectrometry (MS), single quadrupole mass spectrometer (Micromass, Platform model) equipped with an electrospray source is used with a resolution of 0.8 Da at 50% valley.

For Examples 1 to 15 hereafter, the elution conditions corresponding to the results indicated are the following: elution with the acetonitrile-water-trifluoroacetic acid mixture 50-950-0.2 (A) for 1 minute then passing from mixture (A) to an acetonitrile-water mixture 950-50 (B) by a linear gradient over a period of 7.5 minutes before elution with pure mixture B for 2 minutes.

Example 1

5-{[2-(dimethylamino)ethyl]amino}-2-(morpholin-4-ylcarbonyl)-1,3-benzothiazole-4,7-dione 1.1)
5-methoxy-4-nitro-1,3-benzothiazole-2-carboxylic acid 1.1.1)
5-methoxy-4-nitro-1,3-benzothiazole-2-carbaldehyde 12.8 g (0.115 mol; 6 equivalents) of selenium dioxide is added to 4.34 g (19.3 mmol) of 5-methoxy-2-methyl-4-nitro-1,3-benzothiazole in solution in 180 ml of anhydrous dioxane. The reaction mixture is stirred at 80° C. for 18 hours then the insoluble matter is filtered and the solvent is evaporated off under reduced pressure. The expected aldehyde is obtained in the form of a yellow oil and purified on a silica column (eluent:ethyl acetate/heptane:gradient of 30% to 70%). Melting point: 154-155° C.

NMR $^1$H (DMSO d6, 400 MHz, δ): 10.06 (s, 1H, CHO); 8.52-8.49 (d, 1H, arom H); 7.80-7.78 (d, 2H, arom H); 4.04 (s, 3H, OCH$_3$).

1.1.2)
5-methoxy-4-nitro-1,3-benzothiazole-2-carboxylic acid

A solution of 18 g of sodium chlorite and 18 g of sodium hydrogen phosphate in 180 ml of water is added dropwise to the carbaldehyde residue taken up in 420 ml of tert-butanol and 100 ml of 2-methyl-but-2-ene. The reaction mixture is maintained under stirring for 18 hours at ambient temperature, then the insoluble matter is filtered, taken up in water and the aqueous solution obtained is acidified by a 1M solution of hydrochloric acid. The precipitate obtained is filtered and washed with water. The acid is obtained in the form of a beige powder. (m=3.12 g; yield=64%). Melting point: 140-142° C.

NMR $^1$H (DMSO d6, 400 MHz, δ): 8.45-8.43 (d, 1H, arom H); 7.74-7.71 (d, 1H, arom H); 3.99 (s, 3H, CH$_3$).
MS-LC: MH+=254.99; r.t.=8.20 min.

1.2) 5-Methoxy-2-(morpholin-4-ylcarbonyl)-4-nitro-1,3-benzothiazole 980 mg (2.1 mmol; 1.1 eq.) of bromo-tris-pyrrolidino-phosphonium hexafluorophosphate (PyBroP) is added to 500 mg (1.97 mmol) of 5-methoxy-4-nitro-1,3-benzothiazole-2-carboxylic acid and 344 µl (1.97 mmol; 1 eq.) of diisopropylethylamine in solution in 40 ml of dichloromethane. The reaction mixture is maintained for 15 minutes under stirring at ambient temperature, then 202 µl (2.3 mmol; 1.2 eq.) of morpholine and a spatula tip's worth of dimethylaminopyridine are added to the medium which is maintained under stirring for 18 hours at ambient temperature. The insoluble matter is then filtered and the solvent is evaporated off under reduced pressure. The residue is then purified on a silica column (eluent:ethyl acetate/heptane:gradient of 30 to 70% over 40 minutes then for 5 minutes at 70% of ethyl acetate in heptane) and 210 mg (yield=33%) of expected product is obtained in the form of beige powder.

MS-LC: MH+=324.01; r.t.=9.63 min.

1.3) 5-Methoxy-2-(morpholin-4-ylcarbonyl)-1,3-benzothiazol-4-amine 20 mg of 10% palladium on activated carbon is added to 210 mg (0.65 mmol) of 5-methoxy-2-(morpholin-4-ylcarbonyl)-4-nitro-1,3-benzothiazole in solution in 10 ml of methanol. The reaction medium is then placed under stirring under a hydrogen atmosphere for 18 hours. The catalyst is then filtered out and the solvent is evaporated off. 173 mg of the expected product (gross yield=91%) is obtained in the form of a yellow oil and is used in the following stage without other purification.

MS-LC: MH+=294.04; r.t.=9.09 min.

1.4) 5-methoxy-2-(morpholin-4-ylcarbonyl)-1,3-benzothiazole-4,7-dione

A solution of 570 mg (1.063 mmol; 1.8 eq.) of Fremy's salt (potassium nitrosodisulphonate, containing 25 to 50% water and methanol) in a 0.3M aqueous solution of sodium hydrogen phosphate (12 ml) is added dropwise to 173 mg (0.6 mmol) of 5-methoxy-2-(morpholin-4-ylcarbonyl)-1,3-benzothiazol-4-amine in solution in 5 ml of acetone. The reaction mixture is maintained under stirring at ambient temperature for 4 hours, then the acetone is evaporated off and the medium is taken up in 10 ml of dichloromethane and washed twice with 7 ml of a saturated aqueous solution of sodium chloride. The organic phases are combined, dried over magnesium sulphate and the solvent is evaporated off under reduced pressure. 175 mg (gross yield =99%) of expected product is obtained in the form of a yellow powder and is used in the following stage without other purification.

MS-LC: MH+=308.99; r.t.=8.40 min.

1.5) 5-{[2-(dimethylamino)ethyl]amino}-2-(morpholin-4-ylcarbonyl)-1,3-benzothiazole-4,7-dione 66 µl (0.6 mmol; 1 eq.) of N,N-dimethylethylenediamine is added to 175 mg of 5-methoxy-2-(morpholin-4-ylcarbonyl)-1,3-benzothiazole-4,7-dione in solution in 10 ml of anhydrous ethanol. The reaction mixture is stirred at 80° C. for 2 hours then the solvent is evaporated off under reduced pressure. The residue is purified on a silica column (eluent: methanol in dichloromethane: gradient of 0 to 5% over 35 minutes then for 5 minutes at 5% methanol in dichloromethane) and 50 mg (yield=23%) of compound expected is obtained in the form of a red powder. Melting point=207-208° C.

NMR $^1$H (DMSO d6, 400 MHz, δ): 7.56 (t, 1H, NH); 5.61 (s, 1H, CH); 4.24 (m, 2H); 3.69 (m, 6H); 3.26 (m, 2H, CH$_2$); 2.49 (m, 2H, CH$_2$); 2.19 (s, 6H, 2CH$_3$).

MS-LC: MH+=365.06; r.t.=7.19 min.

The compounds of Examples 2 to 13 are obtained according to a protocol analogous to that used for Example 1, with the appropriate amines replacing morpholine in the second stage and with N-(2-aminoethyl)pyrrolidine replacing N,N-dimethylethylenediamine in the last stage for Example 6.

Example 2 tert-butyl {2-[2-(2-{[(5-{[2-(dimethylamino)ethyl]amino}-4,7-dioxo-4,7-dihydro-1,3-benzothiazol-2-yl)carbonyl]amino}ethoxy)ethoxy]ethyl}carbamate Red powder. Melting point: 55-57° C.

NMR $^1$H (DMSO d6, 400 MHz, δ): 9.10 (t, 1H, NH); 7.54 (t, 1H, NH); 6.69 (t, 1H, NH); 5.62 (s, 1H, CH); 3.56-3.43 (m, 8H); 3.37-3.35 (m, 2H); 3.29-3.25 (m, 2H); 3.04-3.02 (m, 2H, CH$_2$); 2.51 (m, 2H, CH$_2$); 2.18 (s, 6H, 2CH$_3$); 1.35 (s, 9H, 3CH$_3$).

MS-LC: MH+=526.34; r.t.=7.80 min.

Example 3

N,N-dibenzyl-5-{[2-(dimethylamino)ethyl]amino}-4,7-dioxo-4,7-dihydro-1,3-benzothiazole-2-carboxamide Red powder.

NMR $^1$H (DMSO d6, 400 MHz, δ): 7.51 (t, 1H, NH); 7.36-7.27 (m, 10H, arom H); 5.61 (s, 1H, CH); 5.26 (s, 2H, CH$_2$); 4.61 (s, 2H, CH$_2$); 3.26-3.23 (m, 2H, CH$_2$); 2.46-2.44 (m, 2H, CH$_2$); 2.17 (s, 6H, 2CH$_3$).

MS-LC: MH+=475.44; r.t.=8.98 min.

Example 4

5-{[2-(dimethylamino)ethyl]amino}-N,N-bis(2-methoxyethyl)-4,7-dioxo-4,7-dihydro-1,3-benzothiazole-2-carboxamide Red powder. Melting point: 92-94° C.

NMR $^1$H (DMSO d6, 400 MHz, δ): 7.53-7.52 (t, 1H, NH); 5.60 (s, 1H, CH); 4.18-4.15 (m, 2H, CH$_2$); 3.69-3.67 (m, 2H, CH$_2$); 3.56-3.53 (m, 4H, 2 CH$_2$); 3.29-3.24 (m, 5H); 3.19 (m, 3H, CH$_3$); 2.48-2.27 (m, 2H, CH$_2$); 2.19 (s, 6H, 2 CH$_3$).

MS-LC: MH+=411.43; r.t.=7.52 min.

Example 5

5-{[2-(dimethylamino)ethyl]amino}-4,7-dioxo-N-[3-(2-oxopyrrolidin-1-yl)propyl]-4,7-dihydro-1,3-benzothiazole-2-carboxamide Red powder. Melting point: 154-156° C.

NMR $^1$H (DMSO d6, 400 MHz, δ): 9.19 (t, 1H, NH); 7.55 (t, 1H, NH); 5.61 (s, 1H, CH); 3.37-3.18 (m, 10H); 2.51-2.49 (m, 2H, CH$_2$); 2.20-2.19 (m, 6H, 2 CH$_3$); 1.93-1.89 (m, 2H, CH$_2$); 1.74-1.69 (m, 2H, CH$_2$).

MS-LC: MH+=420.14; r.t.=7.26 min.

Example 6

4,7-dioxo-N-[3-(2-oxopyrrolidin-1-yl)propyl]-5-[(2-pyrrolidin-1-ylethyl)amino]-4,7-dihydro-1,3-benzothiazole-2-carboxamide Red powder.

NMR $^1$H (DMSO d6, 400 MHz, δ): 9.18 (t, 1H, NH); 7.67 (t, 1H, NH); 5.61 (s, 1H, CH); 3.37-3.18 (m, 10H); 2.68-2.67 (t, 2H, CH$_2$); 2.49 (m, 2H, CH$_2$); 2.20 (t, 2H, CH$_2$); 1.93-1.89 (m, 2H, CH$_2$); 1.74-1.68 (m, 6H).

MS-LC: MH+=446.17; r.t.=7.32 min.

Example 7

5-{[2-(dimethylamino)ethyl]amino}-N-isobutyl-4,7-dioxo-4,7-dihydro-1,3-benzothiazole-2-carboxamide Red powder. Melting point: 163-164° C.

NMR $^1$H (DMSO d6, 400 MHz, δ): 9.21 (t, 1H, NH); 7.54 (t, 1H, NH); 5.61 (s, 1H, CH); 3.28-3.23 (m, 2H, CH$_2$); 3.11-3.08 (m, 2H, CH$_2$); 2.49 (m, 2H, CH$_2$); 2.18 (m, 6H, 2 CH$_3$); 1.92-1.89 (m, 1H, CH); 0.88-0.86 (m, 6H, 2 CH$_3$).

MS-LC: MH+=351.16; r.t.=7.71 min.

Example 8 tert-butyl (4-{[(5-{[2-(dimethylamino)ethyl]amino}-4,7-dioxo-4,7-dihydro-1,3-benzothiazol-2-yl)carbonyl]amino}butyl)carbamate Red powder.

NMR $^1$H (DMSO d6, 400 MHz, δ): 9.21 (t, 1H, NH); 7.54 (t, 1H, NH); 6.77 (t, 1H, NH); 5.61 (s, 1H, CH); 3.28-3.24 (m, 4H, 2CH$_2$); 2.93-2.90 (m, 2H, CH$_2$); 2.49 (m, 2H, CH$_2$); 2.18 (s, 6H, 2CH$_3$); 1.53-1.49 (m, 2H, CH$_2$); 1.39-1.32 (m, 11H).

MS-LC: MH+=466.25; r.t.=7.75 min.

Example 9

5-{[2-(dimethylamino)ethyl]amino}-2-{[4-(2-furoyl)piperazin-1-yl]carbonyl}-1,3-benzothiazole-4,7-dione Red powder.

NMR $^1$H (DMSO d6, 400 MHz, δ): 7.86 (m, 1H, arom H); 7.58 (t, 1H, NH); 7.06 (m, 1H, arom H); 6.64 (m, 1H, arom H); 5.62 (s, 1H, CH); 4.32 (m, 2H); 3.82-3.78 (m, 6H); 3.26-3.25 (m, 2H, CH$_2$); 2.49 (m, 2H, CH$_2$); 2.18 (s, 6H, 2CH$_3$).

MS-LC: MH+=458.08; r.t.=7.39 min.

Example 10

5-{[2-(dimethylamino)ethyl]amino}-N-(2-methoxyethyl)-4,7-dioxo-4,7-dihydro-1,3-benzothiazole-2-carboxamide Red powder.

NMR $^1$H (DMSO d6, 400 MHz, δ): 9.11 (t, 1H, NH); 7.55 (t, 1H, NH); 5.61 (s, 1H, CH); 3.50-3.44 (m, 4H); 3.27-3.24 (m, 5H); 2.49 (m, 2H, CH$_2$); 2.18 (s, 6H, 2CH$_3$).

MS-LC: MH+=353.11; r.t.=7.27 min.

Example 11

N-butyl-5-{[2-(dimethylamino)ethyl]amino}-4,7-dioxo-4,7-dihydro-1,3-benzothiazole-2-carboxamide Red powder.
NMR $^1$H (DMSO d6, 400 MHz, δ): 9.20 (t, 1H, NH); 7.54 (t, 1H, NH); 5.61 (s, 1H, CH); 3.28-3.25 (m, 4H); 2.49 (m, 2H, CH$_2$); 2.18 (s, 6H, 2CH$_3$); 1.54-1.50 (m, 2H, CH$_2$); 1.32-1.27 (m, 2H, CH$_2$); 0.88 (t, 3H, CH$_3$).
MS-LC: MH+=351.10; r.t.=7.78 min.

Example 12

N-benzyl-5-{[2-(dimethylamino)ethyl]amino}-4,7-dioxo-4,7-dihydro-1,3-benzothiazole-2-carboxamide Red powder. Melting point: 188-189° C.
NMR $^1$H (DMSO d6, 400 MHz, δ): 9.78 (t, 1H, NH); 7.55 (t, 1H, NH); 7.34-7.23 (m, 5H, arom H); 5.62 (s, 1H, CH); 4.46-4.45 (m, 2H, CH$_2$); 3.27-3.24 (m, 2H, CH$_2$); 2.49 (m, 2H, CH$_2$); 2.19 (m, 6H, 2 CH$_3$).
MS-LC: MH+=385.09; r.t.=7.89 min.

Example 13

N-(cyclohexylmethyl)-5-{[2-(dimethylamino)ethyl]amino}-4,7-dioxo-4,7-dihydro-1,3-benzothiazole-2-carboxamide Red powder. Melting point: 171-172° C.
NMR $^1$H (DMSO d6, 400 MHz, δ): 9.17 (t, 1H, NH); 7.54 (t, 1H, NH); 5.61 (s, 1H, CH); 3.27-3.24 (m, 2H, CH$_2$); 3.13-3.10 (m, 2H, CH$_2$); 2.49 (m, 2H, CH$_2$); 2.18 (m, 6H, 2 CH$_3$); 1.67-1.60 (m, 6H); 1.22-1.13 (m, 3H); 0.95-0.89 (m, 2H).
MS-LC: MH+=391.13; r.t.=8.23 min.

Example 14

N,N'-(oxydiethane-2,1-diyl)bis(5-{[2-(dimethylamino)ethyl]amino}-4,7-dioxo-4,7-dihydro-1,3-benzothiazole-2-carboxamide)

14.1)
5-methoxy-4-nitro-1,3-benzothiazole-2-carboxylic acid

14.1.1)
5-methoxy-4-nitro-1,3-benzothiazole-2-carbaldehyde 12.8 g (0.115 mol; 6 equivalents) of selenium dioxide is added to 4.34 g (19.3 mmol) of 5-methoxy-2-methyl-4-nitro-1,3-benzothiazole in solution in 180 ml of anhydrous dioxane. The reaction mixture is stirred at 80° C. for 18 hours then the insoluble matter is filtered and the solvent is evaporated off under reduced pressure. The expected aldehyde is obtained in the form of a yellow oil and purified on a silica column (eluent:ethyl acetate/heptane:gradient of 30% to 70%). Melting point: 154-155° C.

NMR $^1$H (DMSO d6, 400 MHz, δ): 10.06 (s, 1H, CHO); 8.52-8.49 (d, 1H, arom H); 7.80-7.78 (d, 2H, arom H); 4.04 (s, 3H, OCH$_3$).

14.1.2)
5-methoxy-4-nitro-1,3-benzothiazole-2-carboxylic acid

A solution of 18 g of sodium chlorite and 18 g of sodium hydrogen phosphate in 180 ml of water is added dropwise to the carbaldehyde residue taken up in 420 ml of tert-butanol and 100 ml of 2-methyl-but-2-ene. The reaction mixture is maintained under stirring for 18 hours at ambient temperature, then the insoluble matter is filtered, followed by taking up in water and the aqueous solution obtained is acidified with a 1M solution of hydrochloric acid. The precipitate obtained is filtered and washed with water. The acid is obtained in the form of a beige powder. (m=3.12 g; yield=64%). Melting point: 140-142° C.

NMR $^1$H (DMSO d6, 400 MHz, δ): 8.45-8.43 (d, 1H, arom H); 7.74-7.71 (d, 1H, arom H); 3.99 (s, 3H, CH$_3$).
MS-LC: MH+=254.99; r.t.=8.20 min.

14.2) N,N'-(oxydiethane-2,1-diyl)bis(5-methoxy-4-nitro-1,3-benzothiazole-2-carboxamide)

3.03 g (6.5 mmol; 1.1 eq.) of bromo-tris-pyrrolidino-phosphonium hexafluorophosphate (PyBroP) is added to 1.5 g (5.9 mmol) of 5-methoxy-4-nitro-1,3-benzothiazole-2-carboxylic acid and 1.13 ml (6.5 mmol; 1.1 eq.) of diisopropylethylamine in solution in 100 ml of dichloromethane. The reaction mixture is maintained for 10 minutes under stirring at ambient temperature, then 0.31 g (2.9 mmol; 0.5 eq.) of 2.2'-oxybis(ethylamine) and a spatula tip's worth of dimethylaminopyridine are added to the medium which is maintained under stirring for 18 hours at ambient temperature. The insoluble matter is filtered and the solvent is evaporated off under reduced pressure. The residue is then purified on a silica column (eluent:ethyl acetate/heptane: 4/1) and 250 mg of expected product (yield=8%) is obtained in the form of beige powder.
MS-LC: MH+=577.11; r.t.=10.27 min.

14.3) N,N'-(oxydiethane-2,1-diyl)bis(4-amino-5-methoxy-1,3-benzothiazole-2-carboxamide)

0.33 g (1.5 mmol; 3.4 eq.) of dihydrated tin chloride is added to 250 mg (0.43 mmol) of N,N'-(oxydiethane-2,1-diyl)bis(5-methoxy-4-nitro-1,3-benzothiazole-2-carboxamide) in solution in 10 ml of concentrated hydrochloric acid. The reaction medium is maintained under stirring at 60° C. for 4 hours, then poured into iced water and neutralized with a 5N soda solution. The expected product is then extracted with 3 times 25 ml of dichloromethane, then the organic phases are combined, dried over magnesium sulphate and the is solvent evaporated off under reduced pressure. 220 mg of the expected product (gross yield=98%) is obtained in the form of a yellow oil and is used in the following stage without other purification.
MS-LC: MH+=517.23; r.t.=9.59 min.

14.4) N,N'-(oxydiethane-2,1-diyl)bis(5-methoxy-4,7-dioxo-4,7-dihydro-1,3-benzothiazole-2-carboxamide)

A solution of 0.91 g (1.7 mmol; 4 eq.) of Fremy's salt (potassium nitrosodisulphonate, containing 25 to 50% of water and methanol) in a 0.3M aqueous solution of sodium hydrogen phosphate (35 ml) is added dropwise to 220 mg (0.43 mmol) of N,N'-(oxydiethane-2,1-diyl)bis(4-amino-5-methoxy-1,3-benzothiazole-2-carboxamide) in solution in 10 ml of acetone. The reaction mixture is maintained under stirring at ambient temperature for 2 hours, then the acetone is evaporated off and the medium is taken up in 25 ml of dichloromethane and washed twice with 15 ml of a saturated aqueous solution of sodium chloride. The organic phases are combined, dried over magnesium sulphate and the solvent is evaporated off under reduced pressure. 230 mg of expected product (gross yield=99%) is obtained in the form of a yellow powder and is used in the following stage without other purification.

MS-LC: MH+=547.12; r.t.=8.76 min.

14.5) N,N'-(oxydiethane-2,1-diyl)bis(5-([2-(dimethylamino)ethyl]amino}-4,7-dioxo-4,7-dihydro-1,3-benzothiazole-2-carboxamide)

81 µl (0.73 mmol; 2 eq.) of N,N-dimethylethylenediamine is added to 200 mg of N,N'-(oxydiethane-2,1-diyl)bis(5-methoxy-4,7-dioxo-4,7-dihydro-1,3-benzothiazole-2-carboxamide) in solution in 300 ml of anhydrous ethanol. The reaction mixture is stirred at 60° C. for 4 hours then the solvent is evaporated off under reduced pressure. The residue is purified on a silica column (eluent: methanol in dichloromethane: gradient of 0 to 20% over 30 minutes then for 15 minutes with 20% of methanol in dichloromethane) and 12 mg (yield=5%) of expected compound is obtained in the form of a red powder.

NMR $^1$H (DMSO d6, 400 MHz, δ): 9.04 (t, 2H, 2NH); 7.49 (t, 2H, 2NH); 5.56 (s, 2H, 2CH); 3.64-3.58 (m, 4H, 2CH$_2$); 3.45-3.41 (m, 4H, 2CH$_2$); 3.26-3.22 (m, 4H, 2CH$_2$); 2.51-2.49 (m, 4H, 2CH$_2$); 2.19 (s, 12H, 4CH$_3$).

MS-LC: MH+=659.20; r.t.=6.99 min.

The compound of Example 15 is obtained according to a protocol analogous to that used for Example 14, with the appropriate amine replacing 2,2'-oxybis(ethylamine) in the second stage.

Example 15

N,N'-[ethane-1,2-diylbis(oxyethane-2,1-diyl)]-bis(5-{[2-(dimethylamino)ethyl]amino}-4,7-dioxo-4,7-dihydro-1,3-benzothiazole-2-carboxamide)

Red powder.
NMR $^1$H (DMSO d6, 400 MHz, δ): 9.07 (t, 2H, 2NH); 7.55 (t, 2H, 2NH); 5.59 (s, 2H, 2CH); 3.57-3.54 (m, 8H, 4CH$_2$); 3.43-3.37 (m, 4H, 2CH$_2$); 3.26-3.22 (m, 4H, 2CH$_2$); 2.50-2.49 (m, 4H, 2CH$_2$); 2.18 (m, 12H, 4CH$_3$).

MS-LC: MH+=703.24; r.t.=7.14 min.

The compounds of Examples 16 to 20 are obtained according to a protocol analogous to that used for Example 1, with the appropriate amines replacing morpholine in the second stage and N-(2-aminoethyl)pyrrolidine replacing N,N-dimethylethylenediamine in the last stage for Example 17.

Example 16

5-{[2-(dimethylamino)ethyl]amino}-2-{[4-(morpholin-4-ylcarbonyl)piperazin-1-yl]carbonyl}-1,3-benzothiazole-4,7-dione Red powder. Melting point: 211-212° C.
NMR $^1$H (DMSO d6, 400 MHz, δ): 7.57 (t, 1H, NH); 5.62 (s, 1H, CH); 4.24 (m, 2H); 3.69 (m, 2H); 3.59-3.56 (m, 4H); 3.30 (m, 4H); 3.19-3.16 (m, 4H); 2.52 (m, 4H); 2.20 (s, 6H, 2CH$_3$).

MS-LC: MH+=477.20; r.t.=7.23 min.

Example 17

2-{[4-(morpholin-4-ylcarbonyl)piperazin-1-yl]carbonyl}-5-[(2-pyrrolidin-1-ylethyl)amino]-1,3-benzothiazole-4,7-dione Red powder. Melting point: 193-194° C.
NMR $^1$H (DMSO d6, 400 MHz, δ): 7.72 (t, 1H, NH); 5.64 (s, 1H, CH); 4.24 (m, 2H); 3.69 (m, 4H); 3.59-3.56 (m, 6H); 3.19-3.16 (m, 6H); 2.66-2.60 (m, 6H); 1.73 (m, 4H).

MS-LC: MH+=503.26; r.t.=7.29 min.

Example 18

5-{[2-(dimethylamino)ethyl]amino}-N-(4-methoxyphenyl)-4,7-dioxo-4,7-dihydro-1,3-benzothiazole-2-carboxamide Red powder. Melting point: 207-208° C.
NMR $^1$H (DMSO d6, 400 MHz, δ): 10.96 (s, 1H, NH); 7.78-7.75 (m, 2H, arom); 7.58 (t, 1H, NH); 6.96-6.93 (m, 2H, arom); 5.65 (s, 1H, CH); 3.75 (s, 3H, OCH$_3$); 3.27-3.26 (m, 2H); 2.53-2.50 (m, 2H); 2.20 (s, 6H, 2CH$_3$).

MS-LC: MH+=401.11; r.t.=7.98 min.

This compound is obtained in salified form, (the salt prepared being a methanesulphonate) according to standard methods known to a person skilled in the art.
Orange powder.
MS-LC: MH+=401.17; r.t.=8.07 min.

Example 19

5-{[2-(dimethylamino)ethyl]amino}-2-{[4-(methylsulphonyl)piperazin-1-yl]carbonyl}-1,3-benzothiazole-4,7-dione Red powder. Melting point: 201-202° C.
NMR $^1$H (DMSO d6, 400 MHz, δ): 7.57 (t, 1H, NH); 5.62 (s, 1H, CH); 4.32 (m, 2H); 3.78 (m, 2H); 3.28-3.25 (m, 6H); 2.91 (s, 3H, CH$_3$); 2.53-2.50 (m, 2H); 2.18 (s, 6H, 2CH$_3$).

MS-LC: MH+=442.15; r.t.=7.31 min.

Example 20

5-{[2-(dimethylamino)ethyl]amino}-2-{[4-(tetrahydrofuran-2-ylcarbonyl)piperazin-1-yl]carbonyl}-1,3-benzothiazole-4,7-dione Red powder. Melting point: 168-169° C.
NMR $^1$H (DMSO d6, 400 MHz, δ): 7.57 (t, 1H, NH); 5.62 (s, 1H, CH); 4.73-4.69 (m, 1H); 4.25-4.21 (m, 2H); 3.79-3.72 (m, 2H); 3.68-3.57 (m, 6H); 3.28-3.25 (m, 2H); 2.51-2.49 (m, 2H); 2.19 (s, 6H, 2CH$_3$); 2.05-2.01 (m, 2H); 1.85-1.80 (m, 2H).

MS-LC: MH+=462.19; r.t.=7.22 min.

Example 21

6-bromo-5-{[2-(dimethylamino)ethyl]amino}-2-{[4-(tetrahydrofuran-2-ylcarbonyl)piperazin-1-yl]carbonyl}-1,3-benzothiazole-4,7-dione 78 mg (0.17 mmol) of the compound of Example 20 is solubilized in 10 mL of acetic acid. 33 mg (0.19 mmol; 1.1 eq.) of N-bromosuccinimide is added and the reaction mixture is agitated for 3 hours at ambient temperature. After concentration under reduced pressure, the residue is purified by chromatography on a silica column (eluent: dichloromethane/methanol 90/10) and the expected product is obtained, after being taken up in ethyl ether, in the form of a violet powder.

Melting point: 161-162° C.

NMR $^1$H (DMSO d6, 400 MHz, δ): 7.47 (t, 1H, NH); 4.73-4.69 (m, 1H); 4.25-4.21 (m, 2H); 3.79-3.72 (m, 2H); 3.68-3.57 (m, 6H); 3.28-3.25 (m, 2H); 2.51-2.49 (m, 2H); 2.19 (s, 6H, 2CH$_3$); 2.05-2.01 (m, 2H); 1.85-1.80 (m, 2H).

MS-LC: MH+=540.09; r.t.=7.39 min.

The compounds of Examples 22 to 26 are obtained according to a protocol analogous to that used for Example 1, with the appropriate amines replacing morpholine in the second stage.

Example 22

5-{[2-(dimethylamino)ethyl]amino}-2-(pyrrolidin-1-ylcarbonyl)-1,3-benzothiazole-4,7-dione Red powder. Melting point: 207-208° C.

NMR $^1$H (DMSO d6, 400 MHz, δ): 7.54 (t, 1H, NH); 5.61 (s, 1H, CH); 4.01 (t, 2H, CH$_2$); 3.55 (t, 2H, CH$_2$); 3.29-3.25 (m, 2H); 2.52-2.49 (m, 2H); 2.19 (s, 6H, 2CH$_3$); 1.98-1.93 (m, 2H); 1.89-1.84 (m, 2H).

MS-LC: MH+=349.16; r.t.=7.45 min.

Example 23

5-{[2-(dimethylamino)ethyl]amino}-2-{[4(2-thienylcarbonyl)piperazin-1-yl]carbonyl}-1,3-benzothiazole-4,7-dione Red powder.

NMR $^1$H (DMSO d6, 400 MHz, δ): 7.79-7.78 (m, 1H); 7.57 (t, 1H, NH); 7.50-7.49 (m, 1H); 7.16-7.13 (m, 1H); 5.62 (s, 1H, CH); 4.33 (m, 2H); 3.79 (m, 6H); 3.28-3.25 (m, 2H); 2.50-2.48 (m, 2H); 2.19 (s, 6H, 2CH$_3$).

MS-LC: MH+=474.15; r.t.=7.55 min.

Example 24

5-{[2-(dimethylamino)ethyl]amino}-N-ethyl-4,7-dioxo-4,7-dihydro-1,3-benzothiazole-2-carboxamide Red powder. Melting point: 174-175° C.

NMR $^1$H (DMSO d6, 400 MHz, δ): 9.21 (t, 1H, NH); 7.54 (t, 1H, NH); 5.61 (s, 1H, CH); 3.27-3.24 (m, 4H); 2.52-2.49 (m, 2H); 2.19 (s, 6H, 2CH$_3$); 1.13 (t, 3H, CH$_3$).

MS-LC: MH+=323.12; r.t.=7.29 min.

Example 25

N-(4-chlorophenyl)-5-{[2-(dimethylamino)ethyl]amino}-4,7-dioxo-4,7-dihydro-1,3-benzothiazole-2-carboxamide Red powder.

NMR $^1$H (DMSO d6, 400 MHz, δ): 11.22 (s, 1H, NH); 7.95-7.85 (m, 3H); 7.46-7.39 (m, 2H); 5.79 (s, 1H, CH); 3.50 (m, 2H); 2.66 (m, 2H); 2.19 (s, 6H, 2CH$_3$).

MS-LC: MH+=405.03; r.t.=8.35 min.

Example 26

N-1,3-benzodioxol-5-yl-5-{[2-(dimethylamino)ethyl]amino}-4,7-dioxo-4,7-dihydro-1,3-benzothiazole-2-carboxamide Red powder. Melting point: 220-221° C.

NMR $^1$H (DMSO d6, 400 MHz, δ): 10.98 (s, 1H, NH); 7.58 (t, 1H, NH); 7.47 (s, 1H); 7.37-7.34 (m, 1H); 6.93-6.91 (m, 1H); 6.02 (s, 2H, CH$_2$); 5.65 (s, 1H, CH); 3.27-3.25 (m, 2H); 2.53-2.51 (m, 2H); 2.19 (s, 6H, 2CH$_3$).

MS-LC: MH+=415.07; r.t.=8.00 min.

The compounds of Examples 27 to 32 are obtained according to a protocol analogous to that used for Example 20, with the appropriate amines replacing N,N-dimethylethylenediamine in the last stage.

Example 27

5-[($^2$-methoxyethyl)amino]-2-{[4-(tetrahydrofuran-2-ylcarbonyl)piperazin-1-yl]carbonyl}-1,3-benzothiazole-4,7-dione Red powder.

MS-LC: MH+=449.16; r.t.=8.16 min.

Example 28

5-(4-methylpiperazin-1-yl)-2-{[4-(tetrahydrofuran-2-ylcarbonyl)piperazin-1-yl]carbonyl}-1,3-benzothiazole-4,7-dione Red powder.

MS-LC: MH+=474.20; r.t.=7.31 min.

Example 29

5-[(2-pyridin-2-ylethyl)amino]-2-{[4-(tetrahydrofuran-2-ylcarbonyl)piperazin-1-yl]carbonyl}-1,3-benzothiazole-4,7-dione Red powder.

MS-LC: MH+=496.20; r.t.=7.42 min.

Example 30

5-[(3-morpholin-4-ylpropyl)amino]-2-{[4-(tetrahydrofuran-2-ylcarbonyl)piperazin-1-yl]carbonyl}-1,3-benzothiazole-4,7-dione Red powder.

MS-LC: MH+=518.22; r.t.=7.34 min.

Example 31

5-[(1-benzylpyrrolidin-3-yl)amino]-2-{[4-(tetrahydrofuran-2-ylcarbonyl)piperazin-1-yl]carbonyl}-1,3-benzothiazole-4,7-dione Red powder.
MS-LC: MH+=550.22; r.t.=7.70 min.

Example 32

5-[(2-cyclohexylethyl)amino]-2-{[4-(tetrahydrofuran-2-ylcarbonyl)piperazin-1-yl]carbonyl}-1,3-benzothiazole-4,7-dione Red powder.
MS-LC: MH+=501.21; r.t.=10.83 min.

The compound of Example 33 is obtained according to a protocol analogous to that used for Example 1, with 4-fluoroaniline replacing morpholine in the second stage.

Example 33

5-{[2-(dimethylamino)ethyl]amino}-N-(4-fluorophenyl)-4,7-dioxo-4,7-dihydro-1,3-benzothiazole-2-carboxamide Red powder. Melting point: 208-209° C.
NMR $^1$H (DMSO d6, 400 MHz, δ): 11.15 (s, 1H, NH); 7.90-7.85 (m, 2H); 7.60 (t, 1H, NH); 7.26-7.20 (m, 1H); 5.66 (s, 1H, CH); 3.27-3.25 (m, 2H); 2.53-2.51 (m, 2H); 2.19 (s, 6H, 2CH$_3$).
MS-LC: MH+=389.14; r.t.=8.11 min.

The compound of Example 34 is obtained according to a protocol analogous to that used for Example 1, with 6-methoxy-2-methyl-7-nitro-1,3-benzothiazole replacing 5-methoxy-2-methyl-4-nitro-1,3-benzothiazole in the first stage and pyrrolidine replacing morpholine in the second stage.

Example 34

6-{[2-(dimethylamino)ethyl]amino}-2-(pyrrolidin-1-ylcarbonyl)-1,3-benzothiazole-4,7-dione Red powder. Melting point: 224-225° C.
NMR $^1$H (DMSO d6, 400 MHz, δ): 7.32 (t, 1H, NH); 5.55 (s, 1H, CH); 4.01 (t, 2H, CH$_2$); 3.55 (t, 2H, CH$_2$); 3.27-3.22 (m, 2H); 2.49-2.47 (m, 2H); 2.18 (s, 6H, 2CH$_3$); 1.98-1.93 (m, 2H); 1.89-1.84 (m, 2H).
MS-LC: MH+=349.16; r.t.=7.35 min.

The compounds of Examples 35 to 37 are obtained according to a protocol analogous to that used for Example 1, with appropriate amine replacing morpholine in the second stage.

Example 35

5-{[2-(dimethylamino)ethyl]amino}-N-(3-fluoro-4-methoxyphenyl)-4,7-dioxo-4,7-dihydro-1,3-benzothiazole-2-carboxamide Red powder. Melting point: 199-200° C.
NMR $^1$H (DMSO d6, 400 MHz, δ): 11.11 (s, 1H, NH); 7.80-7.76 (m, 1H); 7.68-7.66 (m, 1H); 7.60 (t, 1H, NH); 7.21-7.16 (m, 1H); 5.65 (s, 1H, CH); 3.83 (s, 3H, CH$_3$); 3.28-3.26 (m, 2H); 2.53-2.52 (m, 2H); 2.20 (s, 6H, 2CH$_3$).
MS-LC: MH+=419.15; r.t.=8.11 min.

Example 36

5-{[2-(dimethylamino)ethyl]amino}-2-[(6-methoxy-3,4-dihydroquinolin-1(2H)-yl)carbonyl]-1,3-benzothiazole-4,7-dione Red powder. Melting point: 192-193° C.
NMR $^1$H (DMSO d6, 400 MHz, δ): 7.54 (m, 2H); 6.80 (m, 1H); 6.70 (m, 1H); 5.60 (s, 1H, CH); 4.05-4.15 (m, 2H); 3.73 (s, 3H, CH$_3$); 3.27-3.24 (m, 2H); 2.82-2.79 (m, 2H); 2.51-2.49 (m, 2H); 2.18 (s, 6H, 2CH$_3$); 1.98-1.96 (m, 2H).
MS-LC: MH+=441.22; r.t.=8.01 min.

Example 37

5-{[2-(dimethylamino)ethyl]amino}-2-{[4-(4-methoxybenzoyl)piperazin-1-yl]carbonyl}-1,3-benzothiazole-4,7-dione Red powder. Melting point: 209-210° C.
NMR $^1$H (DMSO d6, 400 MHz, δ): 7.60 (t, 1H, NH); 7.44-7.42 (m, 2H); 7.01-6.99 (m, 2H); 5.61 (s, 1H, CH); 4.29-4.31 (m, 2H); 3.80 (s, 3H, CH$_3$); 3.73-3.71 (m, 2H); 3.63.3.61 (m, 4H); 3.28-3.26 (m, 2H); 2.50-2.48 (m, 2H); 2.19 (s, 6H, 2CH$_3$).
MS-LC: MH+=498.30; r.t.=7.73 min.

The compounds of Examples 38 to 39 are obtained according to a protocol analogous to that used for Example 24, with the appropriate amines replacing N,N-dimethylethylenediamine in the last stage.

Example 38

5-[[2-(dimethylamino)ethyl](methyl)amino]-N-ethyl-4,7-dioxo-4,7-dihydro-1,3-benzothiazole-2-carboxamide Red powder. Melting point: 163-164° C.
NMR $^1$H (DMSO d6, 400 MHz, δ): 9.10 (t, 1H, NH); 5.65 (s, 1H, CH); 3.77-3.74 (m, 2H); 3.34-3.32 (m, 2H); 2.98 (s, 3R, CH$_3$); 2.35-2.33 (m, 2H); 1.93 (s, 6R, 2CH$_3$); 1.13 (t, 3H, CH$_3$).
MS-LC: MH+=337.19; r.t.=7.36 min.

Example 39

N-ethyl-5-{[2-(4-fluorophenyl)ethyl]amino}-4,7-dioxo-4,7-dihydro-1,3-benzothiazole-2-carboxamide Red powder. Melting point: 260-261° C.
NMR $^1$H (DMSO d6, 400 MHz, δ): 9.20 (t, 1H, NH); 7.96 (t, 1H, NH); 7.33-7.29 (m, 2H); 7.13-7.09 (m, 2H); 5.66 (s, 1H, CH); 3.44-3.42 (m, 2H); 3.30-3.29 (m, 2H); 2.89 (t, 2H, CH$_2$); 1.13 (t, 3H, CH$_3$).
MS-LC: MH+=374.13; r.t.=10.27 min.

and the salts of these compounds.

Pharmacological Study of the Compounds of the Invention

Test Protocols i) Measurement of the Phosphatase Activity of the Purified Recombinant Enzyme Cdc25C The phosphatase activity of the protein MBP-Cdc25C is evaluated by the dephosphorylation of 3-O-methylfluorescein-phosphate (OMFP) to 3-O-methylfluorescein (OMF)

with a determination of the fluorescence at 475 nm of the reaction product. This test makes it possible to identify inhibitors of the recombinant enzyme cdc25. The preparation of the fusion protein MBP-Cdc25C is described in the Patent Application PCT WO 01/44467.

The reaction is carried out in 384-well plate format at a final volume of 50 µl. The protein MBP-Cdc25C (prepared as described above) is preserved in following elution buffer: 20 mM Tris-HCl pH 7.4; 250 mM NaCl; 1 mM EDTA; 1 mM of dithiothreitol (DTT); 10 mM maltose. It is diluted to a concentration of 60 µM in the following reaction buffer: 50 mM Tris-HCl pH 8.2; 50 mM NaCl; 1 mM DTT; 20% glycerol. Measurement of the background noise is carried out with the buffer without addition of the enzyme. The products are tested at decreasing concentrations starting from 40 µM. The reaction is initiated by the addition of an OMFP solution at 500 µM final (prepared extemporaneously from a 12.5 mM stock solution in 100% DMSO (Sigma #M2629)). After 4 hours at 30° C. in a single-use 384-well plate, the fluorescence measured at OD 475 nm is read using a Victor² plate reader (EGG-Wallac). The determination of the concentration inhibiting the enzyme reaction by 50% is calculated from three independent experiments. Only the values contained in the linear part of the sigmoid are retained for linear regression analysis.

ii) Characterization of Anti-Proliferative Activity:

By way of example, the effect of a treatment by the compounds of the examples described previously on two lines of human Mia-Paca2 and DU145 cells will be studied. The cell lines DU145 (human prostate cancer cells) and Mia-PaCa2 (human pancreatic cancer cells) were acquired from the American Tissue Culture Collection (Rockville, Md., USA). The cells placed in 80 µl of Dulbecco's Modified Eagle medium (Gibco-Brl, Cergy-Pontoise, France) completed with 10% foetal calf serum inactivated by heating (Gibco-Brl, Cergy-Pontoise, France), 50,000 units/l of penicillin and 50 mg/l streptomycin (Gibco-Brl, Cergy-Pontoise, France), and 2 mM of glutamine (Gibco-Brl, Cergy-Pontoise, France) were seeded on a 96-well plate on day 0. The cells were treated on day 1 for 96 hours at increasing concentrations of each of the compounds to be tested up to 10 µM. At the end of the of this period, quantification of the cell proliferation is evaluated by a colorimetric test based on the cleavage of the tetrazolium salt WST1 by the mitochondrial dehydrogenases in the viable cells leading to the formation of formazan (Boehringer Mannheim, Meylan, France). These tests are carried out in duplicate with 8 determinations per concentration tested. For each compound to be tested, the values included in the linear part of the sigmoid were retained for linear regression analysis and used in order to estimate the inhibitory concentration $IC_{50}$. The products are solubilized in dimethylsulphoxide (DMSO) at $10^{-2}$M and finally used in culture with 0.1% DMSO.

Results of the Tests a) The compounds of Examples 1 to 39 have an $IC_{50}$ below or equal to 1.1 µM on the phosphatase activity of the purified recombinant enzyme Cdc25-C.
b) The compounds of the examples 1 to 39 have an $IC_{50}$ below or equal to 10 µM, more particularly below or equal to 4 µM on the cell proliferation of the Mia-Paca2 lines.
c) The compounds of the examples 1 to 39 have an $IC_{50}$ below or equal to 10 µM, more particularly below or equal to 6 µM on the cell proliferation of the DU-145 lines.

The invention claimed is:
1. The compound of general formula (I)

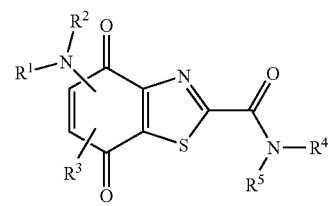

in racemic, enantiomeric form or combination thereof, wherein:
$R^1$ is a hydrogen atom, alkyl, alkoxyalkyl, alkylthioalkyl, cycloalkyl, —(CH$_2$)—X—Y, —(CH$_2$)—Z—NR$^6$R$^7$ radical or a —CHR$^8$R$^9$ radical,
X is a bond or a linear or branched alkylene radical comprising 1 to 5 carbon atoms,
Y is a saturated cyclic carbon system comprising 1 to 3 condensed rings, wherein each ring independently comprises 3 to 7 members, or Y is a saturated heterocycle comprising 1 to 2 heteroatoms including O, N or S and attached to X by an N or CH member, said saturated heterocycle comprising 2 to 6 additional members, each independently including —CHR$^{10}$—, —CO—, —NR$^{11}$—, —O— or —S—, R$^{10}$ is a hydrogen atom or an alkyl radical and R$^{11}$ is a hydrogen atom or an alkyl or aralkyl radical, or Y is a carbocyclic or heterocyclic aryl radical optionally substituted by 1 to 3 substituents including a halogen atom, an alkyl radical, a haloalkyl radical, an alkoxy radical, a haloalkoxy radical, a hydroxy radical, a nitro radical, a cyano radical, a phenyl radical, an SO$_2$NHR$^{12}$ radical or NR$^{13}$R$^{14}$ radical, R$^{12}$ is a hydrogen atom or an alkyl or phenyl radical, and R$^{13}$ and R$^{14}$ are each independently-alkyl radicals,
Z is a bond or a linear or branched alkylene radical comprising 1 to 5 carbon atoms,
R$^6$ and R$^7$ are each independently a hydrogen atom, an alkyl, aralkyl or —(CH$_2$)$_n$—OH radical, wherein n is an integer from 1 to 6,
or R$^6$ is an alkoxycarbonyl, haloalkoxycarbonyl or aralkoxycarbonyl radical and R$^7$ is a hydrogen atom or a methyl radical,
or R$^6$ and R$^7$, together with the nitrogen atom to which they are attached, form a heterocycle with 4 to 7 members comprising 1 to 2 heteroatoms, wherein the members necessary for completing the heterocycle are each independently —CR$^{15}$R$^{16}$—, —O—, —S— or —NR$^{17}$— radicals, R$^{15}$ and R$^{16}$ are each independently a hydrogen atom or an alkyl radical, and R$^{17}$ is a hydrogen atom, an alkyl, or aralkyl radical, or R$^{17}$ is a phenyl radical optionally substituted by 1 to 3 substituents including a halogen atom, an alkyl or alkoxy radical,
R$^8$ and R$^9$, together with the carbon atom to which they are attached, form an indanyl or tetralinyl radical, or R$^8$ and R$^9$, together with the carbon atom to which they are attached, form a saturated heterocycle comprising 5 to 7 members and 1 to 2 heteroatoms including O, N or S, wherein the nitrogen atoms of said heterocycle are optionally substituted by alkyl radicals or a benzyl radical;
R$^2$ is a hydrogen atom, an alkyl radical, or an aralkyl radical;
or R$^1$ and R$^2$, together with the nitrogen atom to which they are attached, form a heterocycle with 4 to 8 members comprising 1 to 2 heteroatoms, wherein the members necessary for completing the heterocycle are each independently —$CR^{18}R^{19}$—, —O—, —S— or —$NR^{20}$— radicals, $R^{18}$ and $R^{19}$ are each independently a hydrogen atom or an alkyl radical, and $R^{20}$ is a hydrogen atom, an alkyl radical, or an aralkyl radical;

$R^3$ represents is a hydrogen atom or a halogen atom;

$R^4$ is an alkyl radical, a haloalkyl radical, a cycloalkyl radical, a cycloalkylalkyl radical, an alkoxyalkyl radical, carbocyclic or heterocyclic aryl radicals or carbocyclic or heterocyclic aralkyl radicals the aryl nucleus of which is optionally substituted by 1 to 3 substituents independently including a halogen atom, an alkyl radical, an alkoxy radical, a haloalkyl radical or —$SO_2$—$NH_2$ radical, or $R^4$ is —$(CH_2)_m$—[O—$(CH_2)_p]_q$—O-Alk, —$(CH_2)_r$—[O—$(CH_2)_s]_t$—$NR^{21}R^{22}$ or —$(CH_2)_v$-A, wherein m, p and s are each independently an integer from 2 to 4, q is an integer from 1 to 4, t is an integer from 0 to 4, r is an integer from 2 to 12 and v is an integer from 1 to 12, Alk is an alkyl radical, $R^{21}$ is a hydrogen atoms, an alkyl, alkoxycarbonyl, or aralkoxycarbonyl radical, $R^{22}$ is a hydrogen atom or an alkyl radical and A is a saturated heterocycle comprising 1 to 2 heteroatoms independently including O, N or S and attached to the —$(CH_2)_v$— group by an N or CH member, said saturated heterocycle including 2 to 6 additional members independently including —$CHR^{23}$—, —CO—, —$NR^{24}$—, —O— or —S—, $R^{23}$ is a hydrogen atom or an alkyl radical and $R^{24}$ is a hydrogen atom, an alkyl radical, an alkoxycarbonyl, or aralkoxycarbonyl group, or $R^4$ is

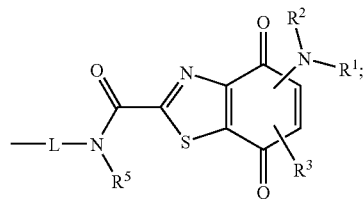

wherein $R^1$, $R^2$, and $R^3$ are as defined above, and L is —$(CH_2)_g$—[O—$(CH_2)_w]_x$—[O—$(CH_2)_y]_z$ or —$(CH_2)_a$-Ω-$(CH_2)_b$—, wherein g, w and y are integers from 2 to 4, x is an integer from 1 to 3 and z is 0 or 1, a and b are independently integers from 2 to 6 and Ω is —O—, —S—, —$NR^{25}$, —CO—, —CO—$NR^{26}$—, —$CR^{27}R^{28}$—, a cycloalkylene radical containing 3 to 7 carbon atoms, or a carbocyclic aryl radical, $R^{25}$ is an alkyl radical, $R^{26}$ is a hydrogen atom or a methyl radical, $R^{27}$ and $R^{28}$ are each independently a hydrogen atom or a methyl group;

or $R^4$ is

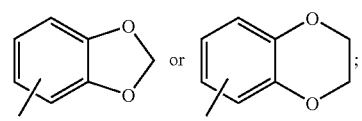

$R^5$ is a hydrogen atom, an alkyl, or aralkyl radical, or $R^5$ is $R^4$ when $R^4$ is a carbocyclic or heterocyclic alkyl, haloalkyl, alkoxyalkyl or aralkyl radical, the aryl nucleus of which is optionally substituted by 1 to 3 substituents independently including a halogen atom, an alkyl radical, an alkoxy radical, a haloalkyl radical or —$SO_2$—$NH_2$ radical;

or $R^4$ and $R^5$, together with the nitrogen atom to which they are attached, form a saturated heterocycle with 4 to 7 members comprising 1 to 2 heteroatoms, wherein the members necessary for completing the heterocycle are each independently —$CR^{29}R^{30}$—, —O—, —S— or —$NR^{31}$—, $R^{29}$ and $R^{30}$ are a hydrogen atom, an alkyl, or aralkyl radical and $R^{31}$ is —$COR^{32}$ or —$SO_2R^{33}$, $R^{32}$ is an alkyl radical, a carbocyclic aryl radical optionally substituted by 1 to 3 substituents including a halogen atom, an alkyl radical, or an alkoxy radical, or $R^{32}$ is a heterocyclic aryl radical or a saturated heterocycle comprising 5 to 7 members and 1 to 2 heteroatoms including O, N or S, $R^{33}$ is a hydrogen atom or an alkyl radical, or $R^4$ and $R^5$, together with the nitrogen atom to which they are attached, form a heterocyclic aryl radical including

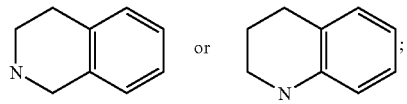

the aromatic ring of which may be substituted by 1 to 3 by substituents including an alkyl radical or an alkoxy radical;

or a salt thereof.

2. Compound according to claim 1, wherein $R^4$ is not

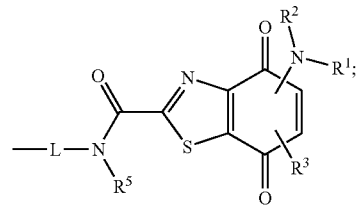

or salt thereof.

3. Compound according to claim 1, wherein $R^4$ is

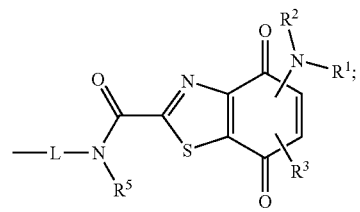

or salt thereof.

4. Compound according to claim 1, wherein the compound is:

5-{[2-(dimethylamino)ethyl]amino}-2-(morpholin-4-ylcarbonyl)-1,3-benzothiazole-4,7-dione;

tert-butyl{2-[2-(2-{[(5-{[2-(dimethylamino)ethyl]amino}-4,7-dioxo-4,7-dihydro-1,3-benzothiazol-2-yl)carbonyl]amino}ethoxy)ethoxy]ethyl}carbamate;

N,N-dibenzyl-5-{[2-(dimethylamino)ethyl]amino}-4,7-dioxo-4,7-dihydro-1,3-benzothiazole-2-carboxamide;

5-{[2-(dimethylamino)ethyl]amino}-N,N-bis(2-methoxyethyl)-4,7-dioxo-4,7-dihydro-1,3-benzothiazole-2-carboxamide;

5-{[2-(dimethylamino)ethyl]amino}-4,7-dioxo-N-[3-(2-oxopyrrolidin-1-yl)propyl]-4,7-dihydro-1,3-benzothiazole-2-carboxamide;

4,7-dioxo-N-[3-(2-oxopyrrolidin-1-yl)propyl]-5-[(2-pyrrolidin-1-ylethyl)amino]-4,7-dihydro-1,3-benzothiazole-2-carboxamide;

5-{[2-(dimethylamino)ethyl]amino}-N-isobutyl-4,7-dioxo-4,7-dihydro-1,3-benzothiazole-2-carboxamide;

tert-butyl(4-{[(5-{[2-(dimethylamino)ethyl]amino}-4,7-dioxo-4,7-dihydro-1,3-benzothiazol-2-yl)carbonyl]amino}butyl)carbamate;

5-{[2-(dimethylamino)ethyl]amino}-2-{[4-(2-furoyl)piperazin-1-yl]carbonyl}-1,3-benzothiazole-4,7-dione;

5-{[2-(dimethylamino)ethyl]amino}-N-(2-methoxyethyl)-4,7-dioxo-4,7-dihydro-1,3-benzothiazole-2-carboxamide;

N-butyl-5-{[2-(dimethylamino)ethyl]amino}-4,7-dioxo-4,7-dihydro-1,3-benzothiazole-2-carboxamide;

N-benzyl-5-{[2-(dimethylamino)ethyl]amino}-4,7-dioxo-4,7-dihydro-1,3-benzothiazole-2-carboxamide;

N-(cyclohexylmethyl)-5-{[2-(dimethylamino)ethyl]amino}-4,7-dioxo-4,7-dihydro-1,3-benzothiazole-2-carboxamide;

N,N'-(oxydiethane-2,1-diyl)bis(5-{[2-(dimethylamino)ethyl]amino}-4,7-dioxo-4,7-dihydro-1,3-benzothiazole-2-carboxamide);

N,N'-[ethane-1,2-diylbis(oxyethane-2,1-diyl)]bis(5-{[2-(dimethylamino)ethyl]amino}-4,7-dioxo-4,7-dihydro-1,3-benzothiazole-2-carboxamide);

5-{[2-(dimethylamino)ethyl]amino}-2-{[4-(morpholin-4-ylcarbonyl)piperazin-1-yl]carbonyl}1,3-benzothiazole-4,7-dione;

2-{[4-(morpholin-4-ylcarbonyl)piperazin-1-yl]carbonyl}-5-[(2-pyrrolidin-1-ylethyl)amino]1,3-benzothiazole-4,7-dione;

5-{[2-(dimethylamino)ethyl]amino}-N-(4-methoxyphenyl)-4,7-dioxo-4,7-dihydro-1,3-benzothiazole-2-carboxamide;

5-{[2-(dimethylamino)ethyl]amino}-2-{[4-(methylsulphonyl)piperazin-1-yl]carbonyl}-1,3-benzothiazole-4,7-dione;

5-{[2-(dimethylamino)ethyl]amino}-2-{[4-(tetrahydrofuran-2-ylcarbonyl)piperazin-1-yl]carbonyl}-1,3-benzothiazole-4,7-dione;

6-bromo-5-{[2-(dimethylamino)ethyl]amino}-2-{[4-(tetrahydrofuran-2-ylcarbonyl)piperazin-1-yl]carbonyl}-1,3-benzothiazole-4,7-dione;

5-{[2-(dimethylamino)ethyl]amino}-2-(pyrrolidin-1-ylcarbonyl)-1,3-benzothiazole-4,7-dione;

5-{[2-(dimethylamino)ethyl]amino}-2-{[4-(2-thienylcarbonyl)piperazin-1-yl]carbonyl}-1,3-benzothiazole-4,7-dione;

5-{[2-(dimethylamino)ethyl]amino}-N-ethyl-4,7-dioxo-4,7-dihydro-1,3-benzothiazole-2-carboxamide;

N-(4-chlorophenyl)-5-{[2-(dimethylamino)ethyl]amino}-4,7-dioxo-4,7-dihydro-1,3-benzothiazole-2-carboxamide;

N-1,3-benzodioxol-5-yl-5-{[2-(dimethylamino)ethyl]amino}-4,7-dioxo-4,7-dihydro-1,3-benzothiazole-2-carboxamide;

5-[(2-methoxyethyl)amino]-2-{[4-(tetrahydrofuran-2-ylcarbonyl)piperazin-1-yl]carbonyl}-1,3-benzothiazole-4,7-dione;

5-(4-methylpiperazin-1-yl)-2-{[4-(tetrahydrofuran-2-ylcarbonyl)piperazin-1-yl]carbonyl}-1,3-benzothiazole-4,7-dione;

5-[(2-pyridin-2-ylethyl)amino]-2-{[4-(tetrahydrofuran-2-ylcarbonyl)piperazin-1-yl]carbonyl}-1,3-benzothiazole-4,7-dione;

5-[(3-morpholin-4-ylpropyl)amino]-2-{[4-(tetrahydrofuran-2-ylcarbonyl)piperazin-1-yl]carbonyl}-1,3-benzothiazole-4,7-dione;

5-[(1-benzylpyrrolidin-3-yl)amino]-2-{[4-(tetrahydrofuran-2-ylcarbonyl)piperazin-1-yl]carbonyl}-1,3-benzothiazole-4,7-dione;

5-[(2-cyclohexylethyl)amino]-2-{[4-(tetrahydrofuran-2-ylcarbonyl)piperazin-1-yl]carbonyl}-1,3-benzothiazole-4,7-dione;

5-{[2-(dimethylamino)ethyl]amino}-N-(4-fluorophenyl)-4,7-dioxo-4,7-dihydro-1,3-benzothiazole-2-carboxamide;

6-{[2-(dimethylamino)ethyl]amino}-2-(pyrrolidin-1-ylcarbonyl)-1,3-benzothiazole-4,7-dione;

5-{[2-(dimethylamino)ethyl]amino}-N-(3-fluoro-4-methoxyphenyl)-4,7-dioxo-4,7-dihydro-1,3-benzothiazole-2-carboxamide;

5-{[2-{dimethylamino)ethyl]amino}-2-[(6-methoxy-3,4-dihydroquinolin-1(2H)-yl)carbonyl]-1,3-benzothiazole-4,7-dione;

5-{(2-(dimethylamino)ethyl]amino}-2-{[4-(4-methoxybenzoyl)piperazin-1-yl]carbonyl}-1,3-benzothiazole-4,7-dione;

5-{[2-(dimethylamino)ethyl](methyl)amino]-N-ethyl-4,7-dioxo-4,7-dihydro-1,3-benzothiazole-2-carboxamide;

N-ethyl-5-{[2-(4-fluorophenyl)ethyl]amino}-4,7-dioxo-4,7-dihydro-1,3-benzothiazole-2-carboxamide;

or salt thereof.

5. A pharmaceutical composition comprising a compound of formula (I) according to claim 1 or a pharmaceutically acceptable salt thereof. according to claim 1 or a pharmaceutically acceptable salt thereof.

6. A pharmaceutical composition comprising, as an active ingredient, a compound of formula (I) according to claim 1 or a pharmaceutically acceptable salt thereof, and at least one pharmaceutically acceptable excipient.

7. A compound according to claim 1, wherein the compound is 5-{[2-(dimethylamino)ethyl]amino}-2-{[4-(2-furoyl)piperazin-1-yl]carbonyl}-1,3-benzothiazole-4,7-dione.

8. A pharmaceutical composition comprising a compound of the formula according to claim 7 or a pharmaceutically acceptable salt thereof.

9. A pharmaceutical composition comprising, as an active ingredient, a compound of the formula according to claim 7 or a pharmaceutically acceptable salt thereof, and at least one pharmaceutically acceptable excipient.

10. A compound according to claim 1, wherein the compound is 6-{[2-(dimethylamino)ethyl]amino}-2-(pyrrolidin-1-ylcarbonyl)-1,3-benzothiazole-4,7-dione.

11. A pharmaceutical composition comprising a compound of the formula according to claim 10 or a pharmaceutically acceptable salt thereof.

12. A pharmaceutical composition comprising, as an active ingredient, a compound of the formula according to claim 10 or a pharmaceutically acceptable salt thereof, and at least one pharmaceutically acceptable excipient.

* * * * *